US012121203B2

(12) United States Patent
Saito

(10) Patent No.: US 12,121,203 B2
(45) Date of Patent: Oct. 22, 2024

(54) ENDOSCOPE SYSTEM

(71) Applicant: FUJIFILM Corporation, Tokyo (JP)

(72) Inventor: Takaaki Saito, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 733 days.

(21) Appl. No.: 17/323,117

(22) Filed: May 18, 2021

(65) Prior Publication Data
US 2021/0267510 A1    Sep. 2, 2021

Related U.S. Application Data

(63) Continuation of application No. PCT/JP2019/047007, filed on Dec. 2, 2019.

(30) Foreign Application Priority Data

Dec. 12, 2018   (JP) .................................. 2018-232822

(51) Int. Cl.
A61B 1/00    (2006.01)
A61B 1/04    (2006.01)
(Continued)

(52) U.S. Cl.
CPC ........ *A61B 1/0005* (2013.01); *A61B 1/00006* (2013.01); *A61B 1/000094* (2022.02);
(Continued)

(58) Field of Classification Search
CPC .............. A61B 1/0005; A61B 1/00006; A61B 1/000094; A61B 1/044; A61B 1/0638;
(Continued)

(56) References Cited

U.S. PATENT DOCUMENTS

2013/0030268 A1   1/2013 Saito
2013/0113906 A1   5/2013 Saito
(Continued)

FOREIGN PATENT DOCUMENTS

CN   102894948 A   1/2013
CN   108289590 A   7/2018
(Continued)

OTHER PUBLICATIONS

An Office Action mailed by China National Intellectual Property Administration on May 31, 2023, which corresponds to Chinese Patent Application No. 201980082745.8 and is related to U.S. Appl. No. 17/323,117; with English language translation.
(Continued)

Primary Examiner — Eric F Winakur
Assistant Examiner — Abid A Mustansir
(74) Attorney, Agent, or Firm — Studebaker & Brackett PC

(57) ABSTRACT

In an endoscope system, an oxygen-saturation-level calculating unit calculates an oxygen saturation level of the observation target on the basis of a plurality of spectral images acquired by an image acquiring unit. An image creating unit creates an oxygen-saturation-level image that is an image representing the oxygen saturation level. A numerical-value display-position determining unit determines a numerical-value display position for displaying a numerical value of the oxygen saturation level on the oxygen-saturation-level image, on the basis of the spectral images or the oxygen saturation level, or the spectral images and the oxygen saturation level. A display control unit displays the numerical value of the oxygen saturation level on the oxygen-saturation-level image on the basis of the numerical-value display position.

9 Claims, 19 Drawing Sheets

(51) Int. Cl.
*A61B 1/06* (2006.01)
*A61B 5/1455* (2006.01)

(52) U.S. Cl.
CPC ............ *A61B 1/044* (2022.02); *A61B 1/0638* (2013.01); *A61B 5/14551* (2013.01)

(58) Field of Classification Search
CPC ............ A61B 5/14551; A61B 5/14503; G06T 2207/10024; G06T 2207/10068; G06T 7/0012; G02B 23/24
See application file for complete search history.

(56) References Cited

U.S. PATENT DOCUMENTS

| | | |
|---|---|---|
| 2014/0031628 A1 | 1/2014 | Kaku |
| 2014/0085686 A1 | 3/2014 | Ishihara |
| 2014/0155717 A1 | 6/2014 | Saito |
| 2017/0135555 A1 | 5/2017 | Yoshizaki |

FOREIGN PATENT DOCUMENTS

| | | |
|---|---|---|
| JP | 2012-130506 A | 7/2012 |
| JP | 2012-249804 A | 12/2012 |
| JP | 2013-022341 A | 2/2013 |
| JP | 2013-099464 A | 5/2013 |
| JP | 2014-023591 A | 2/2014 |
| WO | 2013/035694 A1 | 3/2013 |
| WO | 2017/085793 A1 | 5/2017 |

OTHER PUBLICATIONS

An Office Action mailed by China National Intellectual Property Administration on Nov. 23, 2022, which corresponds to Chinese Patent Application No. 201980082745.8 and is related to U.S. Appl. No. 17/323,117; with English language translation.

An Office Action; "Notice of Reasons for Refusal", mailed by the Japanese Patent Office on Jun. 14, 2022, which corresponds to Japanese Patent Application No. 2020-559173 and is related to U.S. Appl. No. 17/323,117 with English language translation.

International Search Report issued in PCT/JP2019/047007; mailed Feb. 18, 2020.

Written Opinion issued in PCT/JP2019/047007; mailed Feb. 18, 2020.

An Office Action mailed by China National Intellectual Property Administration on Aug. 22, 2022, which corresponds to Chinese Patent Application No. 201980082745.8 and is related to U.S. Appl. No. 17/323,117; with English language translation.

FIG. 9

| SUB-REGION POSITION | BG(i,j) | BG(i,j)≤BG1 |
|---|---|---|
| (1, 1) | – | – |
| (2, 1) | – | – |
| ⋮ | ⋮ | ⋮ |
| (5, 1) | BG(5,1) | N |
| (6, 1) | BG(5,2) | N |
| ⋮ | ⋮ | ⋮ |
| (7, 5) | BG(7,5) | Y |
| (8, 5) | BG(8,5) | Y |
| ⋮ | ⋮ | ⋮ |
| (7, 6) | BG(7, 6) | Y |
| (8, 6) | BG(8, 6) | Y |
| (9, 6) | BG(9, 6) | Y |
| ⋮ | ⋮ | ⋮ |
| (8, 7) | BG(8, 7) | Y |
| (9, 7) | BG(9, 7) | Y |
| ⋮ | ⋮ | ⋮ |
| (16, 16) | – | – |

| SUB-REGION POSITION | SP(i, j) |
|---|---|
| (1, 1) | – |
| (2, 1) | – |
| ⋮ | ⋮ |
| (5, 1) | 99 |
| (6, 1) | 99 |
| ⋮ | ⋮ |
| (7, 5) | 95 |
| (8, 5) | 95 |
| ⋮ | ⋮ |
| (7, 6) | 95 |
| (8, 6) | 92 |
| (9, 6) | 94 |
| ⋮ | ⋮ |
| (8, 7) | 92 |
| (9, 7) | 93 |
| ⋮ | ⋮ |
| (16, 16) | – |

| SPECIFIC REGION POSITION | SP (n-th) |
|---|---|
| FIRST (12, 16)、(16, 16)<br>(12, 12)、(16, 12) | 99 |
| SECOND (7, 16)、(11, 16)<br>(7, 12)、(11, 12) | — |
| ⋮ | ⋮ |

196

ENDOSCOPE SYSTEM

CROSS-REFERENCE TO RELATED APPLICATIONS

This application is a Continuation of PCT International Application No. PCT/JP2019/047007 filed on 2 Dec. 2019, which claims priority under 35 U.S.C § 119(a) to Japanese Patent Application No. 2018-232822 filed on 12 Dec. 2018. The above application is hereby expressly incorporated by reference, in its entirety, into the present application.

BACKGROUND OF THE INVENTION

1. Field of the Invention

The present invention relates to an endoscope system that appropriately displays an oxygen saturation level of an observation target.

2. Description of the Related Art

In the medical field, endoscope systems that image an observation target in a living body are widely used. Among the endoscope systems, some include a normal mode for observing overall properties on a surface of a tissue by irradiating the observation target in a living body with white normal light and a special mode for performing observation by irradiating the observation target with special light. In the special mode, by irradiating an affected area with narrow-band light with limited wavelengths, for example, as the special light, the oxygen saturation level of the observation target is calculated, and an image representing the oxygen saturation level is displayed on a monitor so that the oxygen saturation level of the observation target can be grasped.

As an endoscope system by which distribution of the oxygen saturation level of the observation target can be grasped, an endoscope system is disclosed that creates and displays a highly reliable oxygen-saturation-level image accurately representing the oxygen saturation level of hemoglobin in blood (WO2013/035694A, corresponding to US2014/155717A1). An endoscope system is also disclosed by which the reliability of the oxygen saturation level, which decreases when misalignment occurs, can be visually grasped by changing, when displaying an oxygen-saturation-level image, a method of displaying the oxygen saturation level in accordance with a misalignment amount between a plurality of frame image signals (JP2013-99464A, corresponding to US2013/113906A1).

SUMMARY OF THE INVENTION

The endoscope systems disclosed in WO2013/035694A and JP2013-99464A, which have an oxygen saturation level imaging function, display high and low oxygen saturation levels with pseudo-colors or the like so that the distribution of the oxygen saturation level can be grasped. However, for example, when a subtle difference in the oxygen saturation level between a lesion part and a normal part in the observation target is further desired to be evaluated or the like, it is difficult to grasp the subtle difference in the oxygen saturation level by viewing an image that displays the high and low oxygen saturation levels with pseudo-colors. In addition, by a method of specifying a region of interest with a graphical user interface (GUI) or the like on an oxygen-saturation-level image displayed on a monitor or the like and displaying the numerical value of the oxygen saturation level at the site, an operator's operation may be complex.

Accordingly, an object of the present invention is to provide an endoscope system that appropriately displays the oxygen saturation level of the observation target.

An endoscope system according to the present invention includes an image acquiring unit, an oxygen-saturation-level calculating unit, an image creating unit, a numerical-value display-position determining unit, and a display control unit. The image acquiring unit acquires a plurality of spectral images obtained by imaging of an observation target. The oxygen-saturation-level calculating unit calculates an oxygen saturation level of the observation target on the basis of the plurality of spectral images. The image creating unit creates an oxygen-saturation-level image that is an image representing the oxygen saturation level. The numerical-value display-position determining unit determines a numerical-value display position for displaying a numerical value of the oxygen saturation level on the oxygen-saturation-level image displayed on a display unit, on the basis of either the spectral images or the oxygen saturation level, or both the spectral images and the oxygen saturation level. The display control unit performs control to display the numerical value of the oxygen saturation level on the basis of the numerical-value display position.

For each of a plurality of regions obtained by dividing of the oxygen-saturation-level image, the numerical-value display-position determining unit preferably determines whether the region is the numerical-value display position.

The regions are preferably formed by dividing of the oxygen-saturation-level image in a grid shape.

The numerical-value display-position determining unit preferably calculates a representative value of a signal ratio indicating a pixel value ratio between different spectral images for each of the regions, and, if the representative value of the signal ratio satisfies a signal ratio condition, preferably determines the region to be the numerical-value display position.

The numerical-value display-position determining unit preferably calculates a representative value of the oxygen saturation level in the region, and, if the representative value of the oxygen saturation level satisfies an oxygen-saturation-level condition, determines the region to be the numerical-value display position.

The numerical-value display-position determining unit preferably calculates a representative value of a signal ratio indicating a pixel value ratio between different spectral images for each of the regions and calculates a representative value of the oxygen saturation level in the region, and, if the representative value of the signal ratio satisfies a signal ratio condition, and if the representative value of the oxygen saturation level satisfies an oxygen-saturation-level condition, preferably determines the region to be the numerical-value display position.

The signal ratio condition is preferably that the representative value of the signal ratio is greater than or equal to a signal ratio threshold value or less than or equal to the signal ratio threshold value.

The oxygen-saturation-level condition is preferably that the representative value of the oxygen saturation level is greater than the oxygen saturation level in a periphery of the region by a specific value or more, or is less than the oxygen saturation level in a periphery of the region by a specific value or more.

If the numerical-value display-position determining unit determines the region not to be the numerical-value display position, the numerical-value display-position determining unit preferably determines a specific region that includes the region and that is broader than the region to be the numerical-value display position.

The endoscope system preferably further includes: a light source unit that irradiates the observation target with first illumination light and second illumination light with different spectral characteristics, in which the image acquiring unit preferably acquires a first image signal corresponding to the first illumination light and acquires a second image signal corresponding to the second illumination light whose wavelength range is different from a wavelength range of the first illumination light.

The second illumination light preferably includes different absorption wavelength light for which an absorption coefficient differs between oxyhemoglobin and deoxyhemoglobin.

The endoscope system according to the present invention can appropriately display the oxygen saturation level of the observation target.

BRIEF DESCRIPTION OF THE DRAWINGS

FIG. 9 is a table illustrating a signal ratio condition;

FIG. 12 is a table illustrating numerical values of an oxygen saturation level to be displayed in a unique region;

FIG. 13 is a table illustrating a numerical value of the oxygen saturation level to be displayed in the specific region;

DESCRIPTION OF THE PREFERRED EMBODIMENTS

First Embodiment

Figure 1:
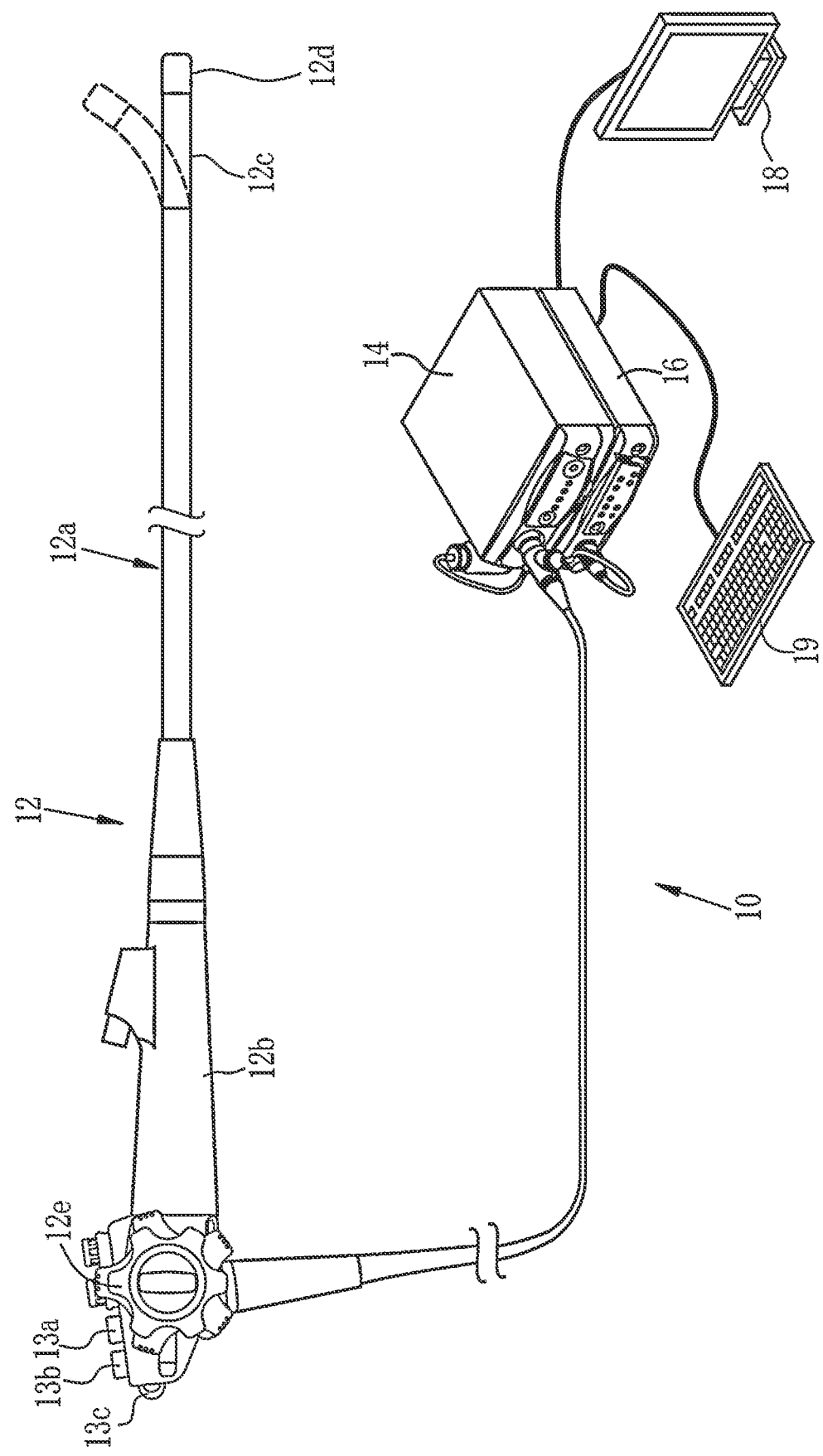
FIG. 1 is an external view of an endoscope system.

As illustrated in FIG. 1, an endoscope system 10 has an endoscope 12, a light source device 14, a processor device 16, a monitor 18 that is a display unit, and a console 19. The endoscope 12 is optically connected to the light source device 14 and is electrically connected to the processor device 16. The endoscope 12 has an insertion part 12a to be inserted into a subject, an operating unit 12b provided at the base end portion of the insertion part 12a, and a bending part 12c and a tip part 12d provided at the distal end side of the insertion part 12a. Operation of an angle knob 12e of the operating unit 12b causes the bending part 12c to bend. As a result of the bending of the bending part 12c, the tip part 12d is oriented in a desired direction. Note that the tip part 12d is provided with a jet orifice (not illustrated) through which air, water, or the like is ejected toward an observation target.

In addition, the operating unit 12b is provided with, in addition to the angle knob 12e, a mode switch 13a, an instruction unit 13b, and a zoom operating unit 13c. The mode switch 13a is used for operation of switching an observation mode. The endoscope system 10 has a normal observation mode and a special observation mode. The normal mode is an observation mode for displaying, on the monitor 18, an image with natural colors (hereinafter referred to as a normal image) obtained by imaging of the observation target by using white light as illumination light.

The special mode is an oxygen-saturation-level observation mode in which an oxygen saturation level of the observation target is calculated and displayed. In the oxygen-saturation-level observation mode, the oxygen saturation level of the observation target is calculated by using a plurality of spectral images obtained by imaging of the observation target, and an image (hereinafter referred to as oxygen-saturation-level image) indicating the value of the calculated oxygen saturation level by using a pseudo-color is generated and displayed on the monitor 18. At this time, in accordance with an instruction from an operator, the numerical value of the oxygen saturation level indicating the oxygen saturation level in a quantitative manner is displayed on the oxygen-saturation-level image.

The instruction unit 13b is used for issuing an instruction for displaying the numerical value of the oxygen saturation level on the oxygen-saturation-level image in the oxygen-saturation-level observation mode. The zoom operating unit 13c is used for operation of displaying the observation target in an enlarged manner or a reduced manner.

The processor device 16 is electrically connected to the monitor 18 and the console 19. The monitor 18 outputs and displays images in the respective observation modes, image information accompanying the images, and the like. The console 19 functions as a user interface that receives an input operation for setting functions and the like. Note that an external recording unit (omitted from illustration) for recording images, image information, and the like may be connected to the processor device 16.

Figure 2:
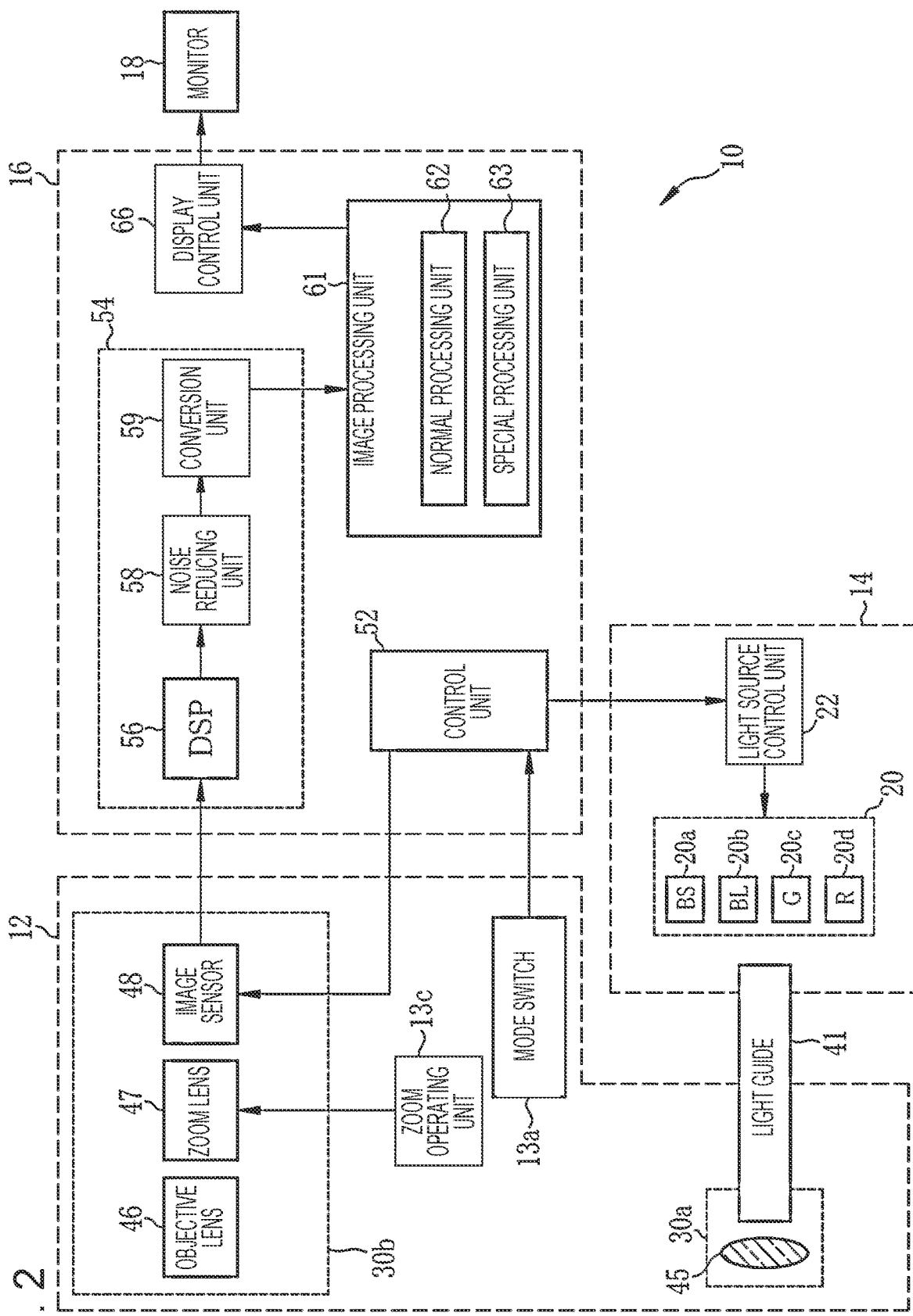
FIG. 2 is a block diagram illustrating functions of the endoscope system.

As illustrated in FIG. 2, the light source device 14 includes a light source unit 20 that emits illumination light and a light source control unit 22 that controls driving of the light source unit 20.

The light source unit 20 includes four light sources, which are a BS light source 20a, a BL light source 20b, a G light source 20c, and an R light source 20d. In this embodiment, the BS light source 20a, the BL light source 20b, the G light source 20c, and the R light source 20d are light emitting diodes (LEDs). For the light source unit 20, instead of these LEDs, a combination of a laser diode (LD), a fluorescent body, and a band limiting filter, a combination of a lamp such as a xenon lamp and a band limiting filter, or the like can be used.

The BS light source 20a is a blue light source that emits first blue light BS with a center wavelength of about 450±10 nm and a wavelength range of about 420 nm to 500 nm. The BL light source 20b is a blue light source that emits blue, so-called narrow-band light (hereinafter referred to as second blue light BL) with a center wavelength and a wavelength range of about 470±10 nm. The G light source 20c is a green light source that emits green light G with a center wavelength of about 540±20 nm and a wavelength range of about 480 nm to 600 nm. The R light source 20d is a red light source that emits red light R with a center wavelength of about 640±20 nm and a wavelength range of about 600 nm to 650 nm.

The light source control unit 22 independently controls timings for turning on and off the respective light sources 20a to 20d constituting the light source unit 20, light emission amounts at the time of turning on, and the like. Under the control of the light source control unit 22, the light source unit 20 emits illumination light for normal observation to be used in the normal observation mode and illumination light for oxygen saturation level observation to be used in the oxygen-saturation-level observation mode.

In a case of the normal observation mode, the light source control unit 22 turns on the BS light source 20a, the G light source 20c, and the R light source 20d at the same time. Accordingly, the illumination light for normal observation is white light including the first blue light BS, the green light G, and the red light R. In this embodiment, although the light source unit 20 constantly emits the above white light in a case of the normal observation mode, the light source unit 20 may emit the white light in accordance with a timing for imaging the observation target (hereinafter referred to as an imaging frame).

Figure 3:
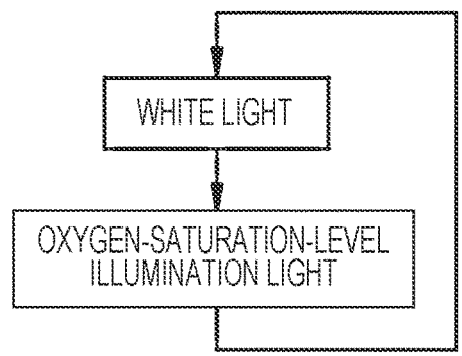
FIG. 3 is an explanation diagram illustrating a first pattern and a second pattern.

In the oxygen-saturation-level observation mode, the light source control unit 22 alternately repeats the turning on and off of the light sources 20a to 20d by using a first pattern and a second pattern. The first pattern is a pattern in which the BS light source 20a, the G light source 20c, and the R light source 20d are turned on at the same time (first illumination light). At the time of the first pattern, white light including the first blue light BS, the green light G, and the red light R is the illumination light. On the other hand, the second pattern is a pattern in which the BL light source 20b, the G light source 20c, and the R light source 20d are turned on at the same time (second illumination light). Accordingly, at the time of the second pattern, illumination light for oxygen saturation level observation includes the second blue light BL, the green light G, and the red light R. In the oxygen-saturation-level observation mode, as illustrated in FIG. 3, the white light and the illumination light for oxygen saturation level observation are alternately and repeatedly emitted in accordance with an imaging frame, for example, for each imaging frame. As described above, spectral characteristics differ between the first illumination light and the second illumination light.

Illumination light emitted from the light source unit 20 enters a light guide 41. The light guide 41 is incorporated in the endoscope 12 and a universal cord (a cord connecting the endoscope 12, the light source device 14, and the processor device 16), and the illumination light propagates therethrough to the tip part 12d of the endoscope 12. Note that a multi-mode fiber can be used as the light guide 41. As an example, a small-diameter fiber cable having a core diameter of 105 μm, a clad diameter of 125 μm, and a diameter of Ø 0.3 to 0.5 mm including a protective layer serving as an outer skin can be used.

The tip part 12d of the endoscope 12 is provided with an illumination optical system 30a and an imaging optical system 30b. The illumination optical system 30a has an illumination lens 45, and the observation target is irradiated with illumination light through the illumination lens 45. The imaging optical system 30b has an objective lens 46, a zoom lens 47, and an image sensor 48. The image sensor 48 images the observation target by using reflected light or the like (including scattered light, fluorescence emitted from the observation target, fluorescence caused by medicine that is, for example, given to the observation target, or the like) of illumination light returning from the observation target through the objective lens 46 and the zoom lens 47. Note that the zoom lens 47 is moved by operation of the zoom operating unit 13c and zooms in or zooms out the observation target to be imaged by the image sensor 48.

Figure 4:
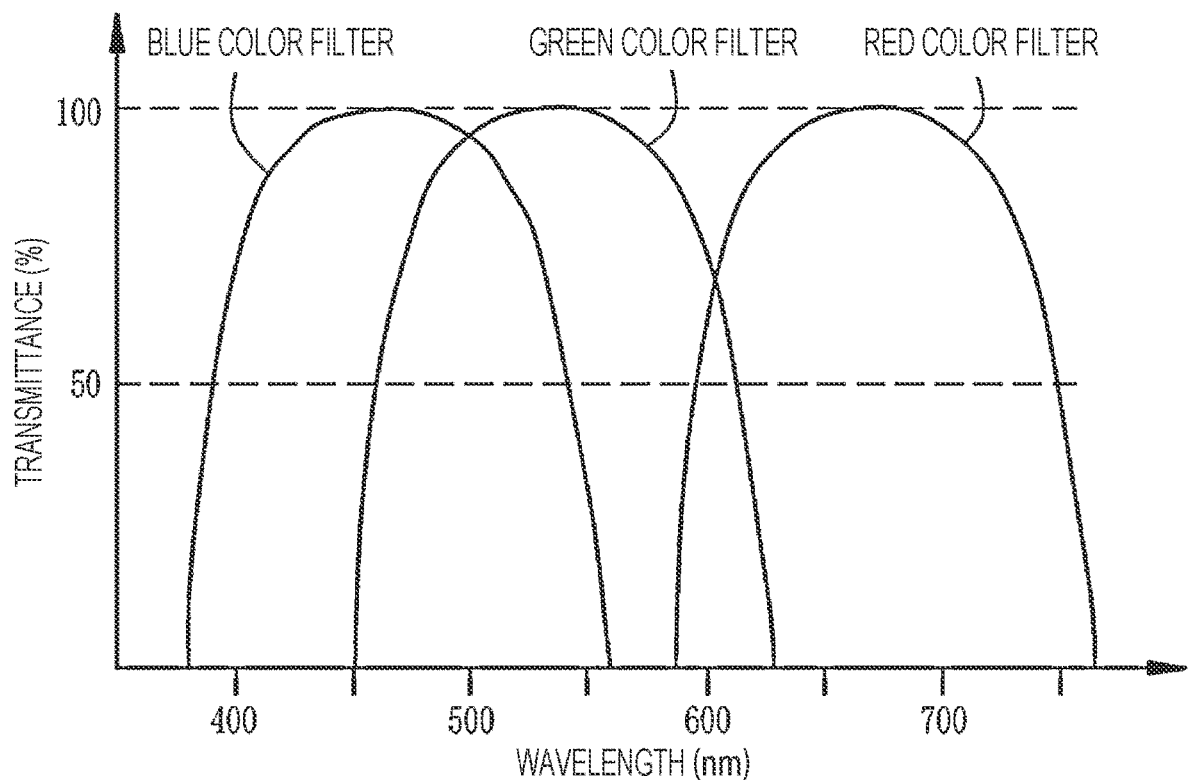
FIG. 4 is a graph illustrating spectral characteristics of color filters.

The image sensor 48 is a color sensor of the primary color system and includes three types of pixels: a B pixel (blue pixel) having a blue color filter, a G pixel (green pixel) having a green color filter, and an R pixel (red pixel) having a red color filter. As illustrated in FIG. 4, the blue color filter mainly transmits light of a blue range, specifically light with a wavelength range of 380 to 560 nm. The transmittance of the blue color filter peaks around a wavelength from 460 to 470 nm. The green color filter mainly transmits light of a green range, specifically light with a wavelength range of 460 to 470 nm. The red color filter mainly transmits light of a red range, specifically light with a wavelength range of 580 to 760 nm.

When the observation target is imaged by the image sensor 48, at most three types of images, which are a B image (blue image) obtained by imaging at the B pixel, a G image (green image) obtained by imaging at the G pixel, and an R image (red image) obtained by imaging at the R pixel, can be obtained in single-time imaging. In a case of the normal observation mode, since the illumination light for normal observation to be used is the white light, a Bc image, a Gc image, and an Rc image are obtained. The Bc image is an image obtained by imaging of the observation target by mainly using, for example, reflected light of the first blue light BS included in the illumination light for normal observation or the like, and the Gc image is an image obtained by imaging of the observation target by mainly using, for example, reflected light of the green light G included in the illumination light for normal observation. Similarly, the Rc image is an image obtained by imaging of the observation target by mainly using, for example, reflected light of the red light R included in the illumination light for normal observation.

On the other hand, in the oxygen-saturation-level observation mode according to this embodiment, illumination light is alternately switched between the white light and the illumination light for oxygen saturation level observation in accordance with the imaging frame. Thus, a B1 image, a G1 image, and an R1 image (first image signal) are acquired by using the white light, and a B2 image, a G2 image, and an R2 image (second image signal) are acquired by using the illumination light for oxygen saturation level observation. The B2 image is an image obtained by imaging of the observation target by mainly using, for example, reflected light of the second blue light BL included in the illumination light for oxygen saturation level observation, and the G2 image is an image obtained by imaging of the observation target by mainly using, for example, reflected light of the green light G included in the illumination light for oxygen saturation level observation. Similarly, the R2 image is an image obtained by imaging of the observation target by mainly using, for example, reflected light of the red light R included in the illumination light for oxygen saturation level observation. Thus, in the oxygen-saturation-level observation mode, spectral images obtained in an imaging frame in which the white light is used as illumination light are the B1 image, the G1 image, and the R1 image, and spectral images obtained in an imaging frame in which the illumination light for oxygen saturation level observation is used as illumination light are the B2 image, the G2 image, and the R2 image.

A charge coupled device (CCD) sensor or a complementary metal oxide semiconductor (CMOS) sensor can be used as the image sensor 48. In addition, although the image sensor 48 in this embodiment is a color sensor of the primary color system, a color sensor of the complementary color system can also be used. The color sensor of the complementary color system has, for example, a cyan pixel provided with a cyan color filter, a magenta pixel provided with a magenta color filter, a yellow pixel provided with a yellow color filter, and a green pixel provided with a green color filter. Images obtained from the pixels of the above respective colors when using the color sensor of the complementary color system can be converted into a B image, a G image, and an R image through complementary color-to-primary color conversion. In addition, instead of the color sensor, a monochrome sensor without a color filter can be used as the image sensor 48. In this case, by sequentially imaging the observation target by using illumination light of the respective colors such as BGR, images of the above respective colors can be obtained.

The processor device 16 has a control unit 52, an image acquiring unit 54, an image processing unit 61, and a display control unit 66.

In response to an input of a mode switching signal from the mode switch 13a, the control unit 52 inputs a control signal into the light source control unit 22 and the image sensor 48 to switch the observation mode. Besides, the control unit 52 controls synchronization of an illumination-light irradiation timing and an imaging timing, for example.

The image acquiring unit 54 acquires images of the observation target from the image sensor 48. In a case of the normal observation mode, the image acquiring unit 54 acquires the Bc image, the Gc image, and the Rc image in each imaging frame. In a case of the oxygen-saturation-level observation mode, the image acquiring unit 54 acquires the B1 image, the G1 image, and the R1 image in an imaging frame in which the white light is used as illumination light, and acquires the B2 image, the G2 image, and the R2 image in an imaging frame in which the illumination light for oxygen saturation level observation is used as illumination light.

In addition, the image acquiring unit 54 has a digital signal processor (DSP) 56, a noise reducing unit 58, and a conversion unit 59 and performs various kinds of processing on the acquired images by using these units.

The DSP 56 performs various kinds of processing on the acquired images, such as defect correction processing, offset processing, gain correction processing, linear matrix processing, gamma conversion processing, demosaicing processing, and YC conversion processing, as needed.

The defect correction processing is processing for correcting the pixel value of a pixel corresponding to a defective pixel of the image sensor 48. The offset processing is processing for setting an accurate zero level by reducing a dark current component from an image subjected to the defect correction processing. The gain correction processing is processing for adjusting the signal level of each image by multiplying the image subjected to the offset processing by a gain. The linear matrix processing is processing for increasing the color reproducibility of an image subjected to the offset processing, and the gamma conversion processing is processing for adjusting the brightness and saturation of an image subjected to the linear matrix processing. The demosaicing processing (also referred to as isotropic processing or synchronization processing) is processing for interpolating the pixel value of a lacking pixel and is performed on an image subjected to the gamma conversion processing. The lacking pixel is a pixel without a pixel value as a result of arrangement of a pixel of another color in the image sensor 48 for the array of the color filters. For example, since the B image is an image obtained by imaging of the observation target at the B pixel, there are no pixel values of pixels at positions corresponding to the G pixel and the R pixel in the image sensor 48. The demosaicing processing interpolates the B image and generates the pixel values of the pixels at positions of the G pixel and the R pixel in the image sensor 48. The YC conversion processing is processing for converting an image subjected to the demosaicing processing into a luminance channel Y, a chrominance channel Cb, and a chrominance channel Cr.

The noise reducing unit 58 performs noise reducing processing on the luminance channel Y, the chrominance channel Cb, and the chrominance channel Cr by using, for example, a moving average method, a median filter method, or the like. The conversion unit 59 re-converts the luminance channel Y, the chrominance channel Cb, and the chrominance channel Cr, which have been subjected to the noise reducing processing, into images of BGR colors again.

The image processing unit 61 has a normal processing unit 62 and a special processing unit 63. The normal processing unit 62 operates in the normal observation mode and performs color converting processing, color emphasizing processing, and structure emphasizing processing on the Bc image, the Gc image, and the Rc image in an imaging frame, which have been subjected to any of the above types of processing, to generate a normal image. In the color converting processing, the images of BGR colors are subjected to 3×3 matrix processing, gradation transformation processing, three-dimensional look-up table (LUT) processing, and the like. The color emphasizing processing is processing for emphasizing the colors in an image, and the structure emphasizing processing is, for example, processing for emphasizing a tissue or a structure of the observation target, such as a blood vessel or a pit pattern. The display control unit 66 sequentially acquires normal images from the normal processing unit 62 and converts the acquired normal images into a format suitable for display to sequentially output and display the normal images to/on the monitor 18. Thus, in a case of the normal observation mode, a physician or the like can observe the observation target by using a moving image of the normal images.

Figure 5:
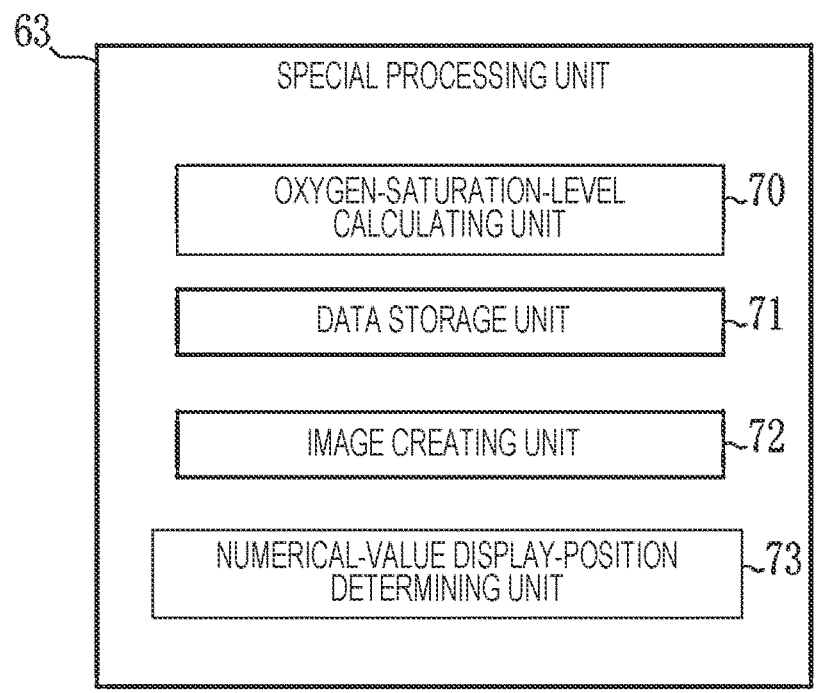
FIG. 5 is a block diagram illustrating functions of a special processing unit.

As illustrated in FIG. 5, the special processing unit 63 includes an oxygen-saturation-level calculating unit 70, a data storage unit 71, an image creating unit 72, and a numerical-value display-position determining unit 73.

The oxygen-saturation-level calculating unit 70 acquires captured images obtained in the oxygen-saturation-level observation mode from the image acquiring unit 54, and by using these captured images, obtains computation values and calculates the oxygen saturation level. More specifically, the oxygen-saturation-level calculating unit 70 acquires the B1 image, the G1 image, the R1 image, the B2 image, the G2 image, and the R2 image as spectral images at the time of the oxygen-saturation-level observation mode from the image acquiring unit 54. Subsequently, the oxygen-saturation-level calculating unit 70 calculates a ratio B2/(B1+G1) of the B2 image to the sum of the B1 image and the G1 image and a ratio R1/G1 of the R1 image to the G1 image for each pixel. These ratios (signal ratios) B2/(B1+G1) and R1/G1 are computation values to be used for calculating the oxygen saturation level.

Figure 6:
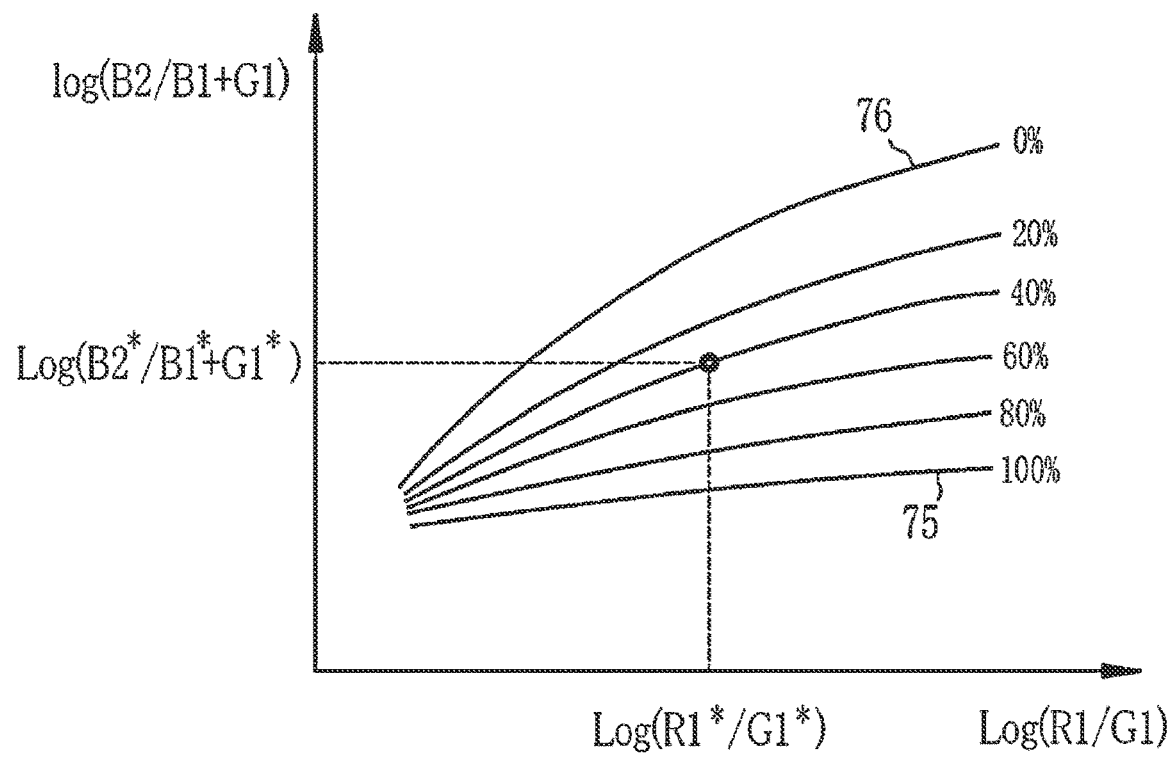
FIG. 6 illustrates a feature space representing a correlation between a computation value and an oxygen saturation level.

The data storage unit 71 stores a correlation between the above computation values and the oxygen saturation level calculated by the oxygen-saturation-level calculating unit 70 in the form of an LUT or the like. As illustrated in FIG. 6, when the correlation is represented in a first feature space formed by using a vertical axis Log B2/(B1+G1) and a horizontal axis Log (R1/G1), isopleths each connecting points of the same oxygen saturation level are formed in substantially the lateral direction. In addition, as the oxygen saturation level is higher, the isopleth is located lower in the vertical axis direction. For example, an isopleth 75 representing a 100% oxygen saturation level is located below an isopleth 76 representing a 0% oxygen saturation level.

Figure 7:
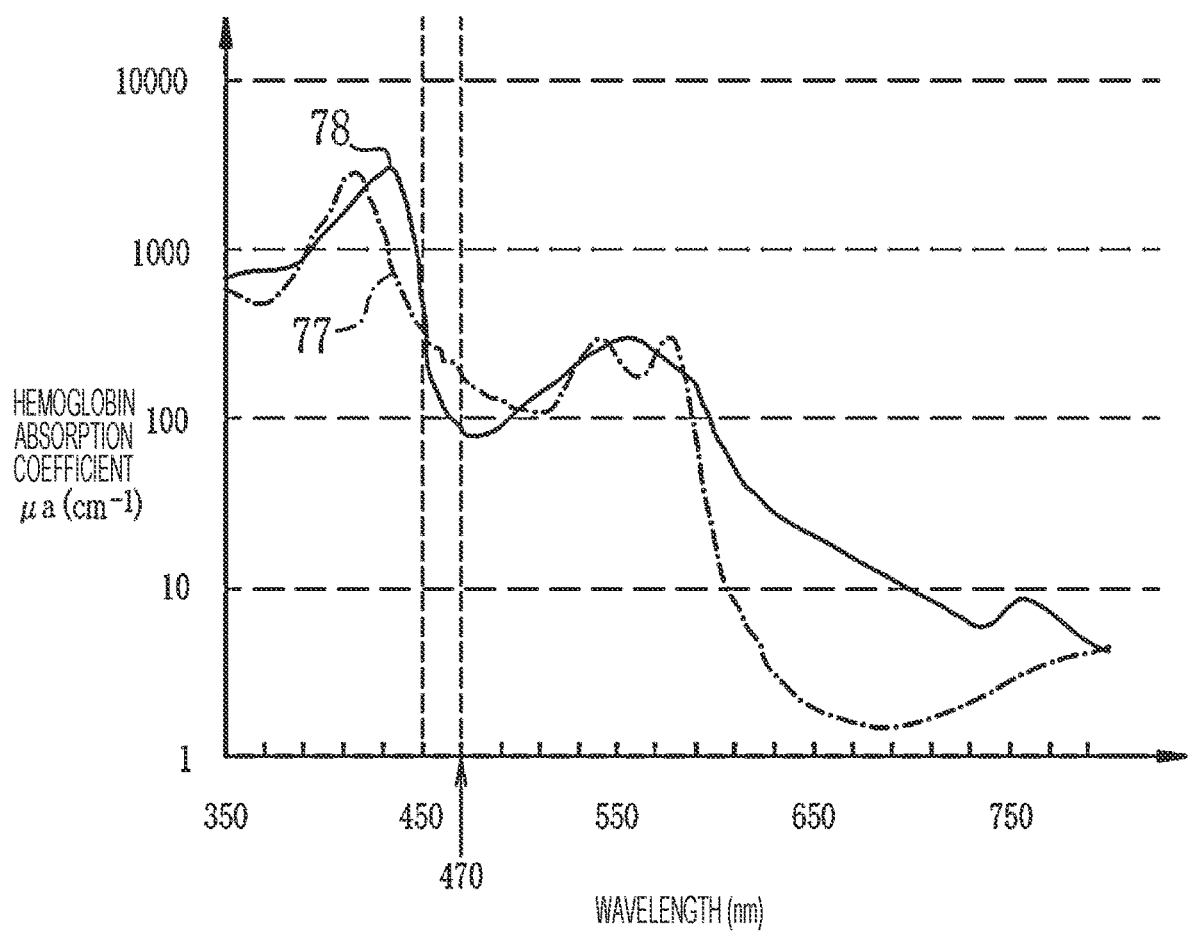
FIG. 7 is a graph illustrating absorption coefficients of oxyhemoglobin and deoxyhemoglobin.

The above correlation is closely related to absorption characteristics of oxyhemoglobin (graph 77) and deoxyhemoglobin (graph 78) illustrated in FIG. 7. Specifically, the wavelength (about 470±10 nm) of the second blue light BL has a large difference between the absorption characteristics of oxyhemoglobin and the absorption characteristics of deoxyhemoglobin. Thus, the absorption amount changes depending on the oxygen saturation level of hemoglobin. That is, the second blue light BL is different absorption wavelength light for which the absorption coefficient differs between oxyhemoglobin and deoxyhemoglobin. Accordingly, it is easy to handle the information about the oxygen saturation level by using the second blue light BL. Therefore, the oxygen saturation level can be calculated by using the ratio B2/(B1+G1) for standardizing the B2 image by using the B1 image and the G1 image for correcting uneven illuminance or the like. However, the ratio B2/(B1+G1) is dependent on, not only the oxygen saturation level, but also the blood volume. Therefore, in addition to the ratio B2/(B1+G1), by using the ratio R1/G1 that changes mainly depending on the blood volume, the oxygen saturation level can be calculated without being influenced by the blood volume. Note that the wavelength (about 540±20 nm) of the green light G included in the G1 image has a comparatively high hemoglobin absorption coefficient, and thus, the absorption coefficient easily changes depending on the blood volume. Note that the position and shape of isopleths in the above first feature space are obtained in advance as a result of a physical simulation of light scattering.

Referring to the data stored in the data storage unit 71, the oxygen-saturation-level calculating unit 70 calculates the oxygen saturation level. In this embodiment, specifically, referring to the correlation stored in the data storage unit 71, the oxygen-saturation-level calculating unit 70 calculates the oxygen saturation level corresponding to the ratio B2/(B1+G1) and the ratio R1/G1 for each pixel. For example, referring to the correlation stored in the data storage unit 71, the oxygen saturation level corresponding to a ratio B2*/(B1*+G1*) and a ratio R1*/G1* for a specific pixel is "40%" (see FIG. 6). Accordingly, the oxygen-saturation-level calculating unit 70 calculates the oxygen saturation level in this specific pixel as "40%".

Note that the ratio B2/(B1+G1) and the ratio R1/G1 are unlikely to become extremely high or extremely low. That is, the combination of values of the ratio B2/(B1+G1) and the ratio R1/G1 is unlikely to be distributed below the isopleth 75 (see FIG. 6), which is the upper limit of the 100% oxygen saturation level, or, in contrast, above the isopleth 76 (see FIG. 6), which is the lower limit of the 0% oxygen saturation level. If, by any possibility, the combination of values of the ratio B2/(B1+G1) and the ratio R1/G1 is distributed below the isopleth 75, which is the upper limit, the oxygen-saturation-level calculating unit 70 calculates the oxygen saturation level of the pixel as 100%. Similarly, if the combination of values of the ratio B2/(B1+G1) and the ratio R1/G1 is distributed above the isopleth 76, which is the lower limit, the oxygen-saturation-level calculating unit 70 calculates the oxygen saturation level of the pixel as 0%. In addition, if points corresponding to the ratios B2/(B1+G1) and R1/G1 are not distributed between the upper limit isopleth 75 and the lower limit isopleth 76, the low reliability of the oxygen saturation level in this pixel may be displayed, or the oxygen saturation level may not be calculated.

By using the oxygen saturation level calculated by the oxygen-saturation-level calculating unit 70, the image creating unit 72 generates an oxygen-saturation-level image that is an image representing the oxygen saturation level. Specifically, the image creating unit 72 acquires the B1 image, the G1 image, and the R1 image and multiplies these images by gains in accordance with the oxygen saturation level pixel by pixel. For example, for a pixel in which the oxygen saturation level is 60% or more, the image creating unit 72 multiplies each of the B1 image, the G1 image, and the R1 image by the same gain "1". In contrast, for a pixel in which the oxygen saturation level is less than 60%, the image creating unit 72 multiplies the B1 image by a gain less than "1" and multiplies the G1 image and the R1 image by a gain greater than or equal to "1". Subsequently, the image creating unit 72 generates a color oxygen-saturation-level image by using the B1 image, the G1 image, and the R1 image multiplied by the gains as described above. Oxygen-saturation-level images generated by the image creating unit 72 are acquired by the display control unit 66 and are sequentially displayed on the monitor 18.

In an oxygen-saturation-level image generated by the image creating unit 72, a high-oxygen region (region where the oxygen saturation level is 60% or more and 100% or less in this embodiment) has natural colors as in the normal image. On the other hand, in a low-oxygen region where the oxygen saturation level is below a preset value (where the oxygen saturation level is 0% or more and less than 60% in this embodiment), in accordance with the calculated oxygen saturation level, colors are different from those of the normal image (so-called pseudo-colors). Note that the image creating unit 72 performs gain multiplication for providing pseudo-colors in only the low-oxygen region in a case of the oxygen-saturation-level observation mode in this embodiment. However, also in the high-oxygen region, the image creating unit 72 may perform gain multiplication in accordance with the oxygen saturation level for providing pseudo-colors in the entire oxygen-saturation-level image. In addition, although the boundary between the low-oxygen region and the high-oxygen region is the oxygen saturation level being 60%, this the boundary may be set to any value.

The numerical-value display-position determining unit 73 determines a numerical-value display position for displaying the numerical value of the oxygen saturation level on the oxygen-saturation-level image displayed on the monitor 18, on the basis of either the plurality of spectral images obtained by imaging from the image acquiring unit 54 or the oxygen saturation level obtained from the oxygen-saturation-level calculating unit 70, or both the spectral images and the oxygen saturation level. More specifically, by using the spectral images or the oxygen saturation level, or both, the numerical-value display-position determining unit 73 first designates, as the numerical-value display position, a region (hereinafter referred to as assumed region of interest) in the oxygen-saturation-level image where the numerical value of the oxygen saturation level is considered to be useful for diagnosis or the like.

The assumed region of interest can be a unique region in the oxygen-saturation-level image and is, for example, a region where a blood vessel structure or the like or the numerical value of the oxygen saturation level differs from that in the periphery. The numerical-value display-position determining unit 73 determines the display position of the numerical value of the oxygen saturation level in a stepwise manner First, the numerical-value display position is determined in the assumed region of interest. Then, the numerical-value display position is determined in a region other than the region that is determined as the numerical-value display position in the assumed region of interest.

The numerical-value display-position determining unit 73 operates in response to single-time pressing of the instruction unit 13b (see FIG. 1) of the endoscope 12 in the oxygen-saturation-level observation mode and automatically performs the following processing. By the processing performed by the numerical-value display-position determining unit 73, the oxygen-saturation-level image (FIG. 15) on which the numerical values of the oxygen saturation level are displayed on the basis of the numerical-value display positions is displayed on the monitor 18.

As a method of determining the numerical-value display position in the oxygen-saturation-level image, the numerical-value display-position determining unit 73 divides the oxygen-saturation-level image into a plurality of regions (hereinafter referred to as sub-regions). For each of the plurality of sub-regions divided from the oxygen-saturation-level image, the numerical-value display-position determining unit 73 determines whether the sub-region is the numerical-value display position. In this embodiment, the sub-regions are formed by dividing of the oxygen-saturation-level image in a grid shape. Thus, although the sub-regions are in a grid shape in this embodiment, the shape of the sub-regions can be determined to be any shape. Note that, if, for example, a sub-region is in a part out of scope, a problem may occur as a target of various calculations for determining the numerical-value display position. Such a case may be determined by image processing or the like, and the sub-region may be excluded from the target of various calculations for determining the numerical-value display position and may not be set as the numerical-value display position.

Figure 8:
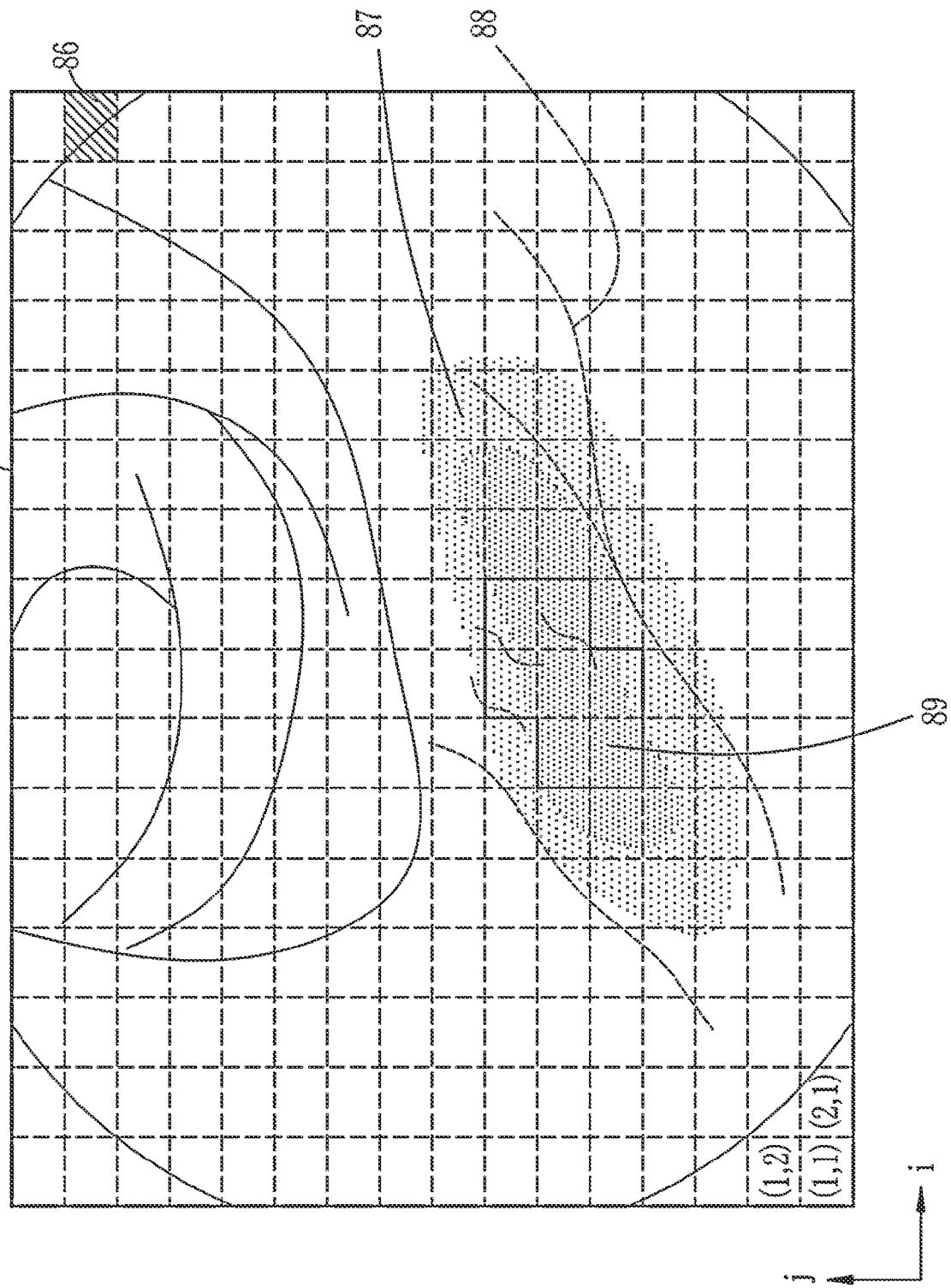
FIG. 8 is an explanation diagram illustrating dividing of an oxygen-saturation-level image.

As illustrated in FIG. 8, as for the sub-regions in a grid shape, more specifically, a region obtained when an oxygen-saturation-level image 85 is divided in the form of a grid of 16 in height and 16 in width is a sub-region 86. The oxygen-saturation-level image 85 includes a low-oxygen region 87 and a blood vessel 88 displayed with pseudo-colors. Since the oxygen-saturation-level image 85 in this embodiment is an image with 640 pixels in width and 480 pixels in height, dividing the oxygen-saturation-level image 85 generates 256 grid-like sub-regions 86 in the same shape, each with 40 pixels in width and 30 pixels in height. On the oxygen-saturation-level image 85, a number indicating the horizontal position in the grid is sequentially counted from the left starting from 1, a number indicating the vertical position in the grid is sequentially counted from the bottom starting from 1, and the position of any given sub-region is (i,j). Thus, as illustrated in FIG. 8, the oxygen-saturation-level image 85 is divided into 256 sub-regions 86 from a sub-region (1,1) to a sub-region (16,16). In FIG. 8, to simplify the figure, the number indicating the position of the sub-region is given for only the sub-region (1,1), the sub-region (2,1), and the sub-region (1,2).

The numerical-value display-position determining unit 73 first determines the numerical-value display position in the assumed region of interest. In this embodiment, the assumed region of interest is a region where a superficial blood vessel density is high. In the region where the superficial blood vessel density is high, the value of a signal ratio B1/G1 using the B1 image and the G1 image in the spectral images acquired by the image acquiring unit 54 tends to be small. Thus, the numerical-value display-position determining unit 73 calculates a representative value of the signal ratio indicating a pixel value ratio between different spectral images for each of the sub-regions, and, if the representative value of the signal ratio satisfies a signal ratio condition, determines the sub-region to be the numerical-value display position. For each of the sub-regions, the numerical-value display-position determining unit 73 determines whether the sub-region is the numerical-value display position. In the sub-region determined to be the numerical-value display position, a single numerical value of the oxygen saturation level is displayed.

To determine the numerical-value display position in the region where the superficial blood vessel density is high, the numerical-value display-position determining unit 73 calculates a representative value of the signal ratio B1/G1 for each of all sub-regions (i,j), and, if the representative value of the signal ratio B1/G1 satisfies the signal ratio condition, determines the sub-region to be the numerical-value display position as a sub-region where the superficial blood vessel density is particularly high. Note that the representative value of the signal ratio B1/G1 in a sub-region (i,j) is a representative value BG (i,j).

The representative value BG (i,j) is determined as follows. That is, signal ratios B1/G1 are calculated in all the pixels that a sub-region (i,j) has in the oxygen-saturation-level image 85, and the average value of these signal ratios B1/G1 in the sub-region (i,j) is calculated. This average value is set as the representative value BG (i,j).

The signal ratio condition is that the representative value of the signal ratio is less than or equal to a signal ratio threshold value. Thus, the representative value BG (i,j) of the signal ratio and a preset signal ratio threshold value BG1 are compared with each other, and, if the representative value BG (i,j) is less than or equal to the threshold value BG1, the signal ratio condition is satisfied. Note that the signal ratio condition may be, depending on the case, that the representative value BG (i,j) is greater than or less than the threshold value BG1 or that the representative value BG (i,j) is greater than or equal to the threshold value BG1 or less than or equal to the threshold value BG1. The numerical-value display-position determining unit 73 examines whether the signal ratio condition is satisfied in all sub-regions (i,j).

In this embodiment, a sub-region (i,j) that satisfies the signal ratio condition that the representative value BG (i,j) is less than or equal to the threshold value BG1, that is, the signal ratio condition of the representative value BG (i,j) ≤the threshold value BG1, is set as the numerical-value display position. Thus, the sub-region (i,j) set as the numerical-value display position is set as a unique region. For sub-regions (i,j) such as the sub-region (1,1), the sub-region (1,2), . . . , the representative value BG (i,j) is calculated. On the basis of the signal ratio condition, by comparing the value of the calculated representative value BG (i,j) with the threshold value BG1, a sub-region where the representative value BG (i,j) is less than or equal to the threshold value BG1 is set as the unique region.

More specifically, a table 90 in FIG. 9 illustrates the sub-region (i,j), the representative value BG (i,j) in the sub-region (i,j), and whether the signal ratio condition (representative value BG (i,j)≤threshold value BG1) is satisfied ("Y" in the cell "BG (i,j)≤threshold value BG1" in the table 90) or not satisfied ("N" or "–" in the cell "BG (i,j)≤threshold value BG1" in the table 90) in the sub-region (i,j). Although only some sub-regions (i,j) are illustrated in the table 90 to avoid complexity, in fact, determination of the signal ratio condition is performed for all sub-regions (i,j).

As illustrated in the table 90 (FIG. 9), since the sub-region (1,1), the sub-region (2,1), and the sub-region (16,16) are determined to be out of scope, the representative value BG (i,j) is not calculated, and the cell "BG (i,j) BG1" in the table 90 is marked as "–". For the sub-region (5,1) and the sub-region (6,1), although the representative value BG (i,j) is calculated, the signal ratio condition of BG (i,j) BG1 is not satisfied, and thus, the sub-region (5,1) and the sub-region (6,1) are not the unique region, and the cell "BG (i,j) BG1" in the table 90 is marked as "N". For the sub-region (7,5) and the sub-region (8,5), the representative value BG (i,j) is calculated, and the signal ratio condition of BG (i,j) BG1 is satisfied, and thus, the sub-region (7,5) and the sub-region (8,5) are the unique region, and the cell "BG (i,j)≤BG1" in the table 90 is marked as "Y". Thus, on the oxygen-saturation-level image 85, the positions of the sub-region (7,5), the sub-region (8,5), the sub-region (7,6), the sub-region (8,6), the sub-region (9,6), the sub-region (8,7), and the sub-region (9,7) are determined as a unique region 89. In the sub-regions that are the unique region 89, the numerical value of the oxygen saturation level in each of the sub-regions is displayed.

The numerical value of the oxygen saturation level to be displayed in the sub-region will be described. In this embodiment, the numerical value of the oxygen saturation level to be displayed is an average value SP (i,j) of the oxygen saturation level calculated in all the pixels included in the sub-regions (i,j) included in the unique region. Since the unique region is set in units of sub-region (i,j), the average value SP of the oxygen saturation level calculated in all the pixels included in a single sub-region (i,j) is the numerical value of the oxygen saturation level to be displayed in the unique region.

A table 195 in FIG. 12 illustrates the sub-region (i,j) (cell "sub-region position" in the table 195) and the average value SP (i,j) of the oxygen saturation level (cell "SP (i,j)" in the table 195). For example, the numerical value 95, which is the average value SP (7,5) of the oxygen saturation level in the sub-region (7,5), and the numerical value 95, which is the average value SP (8,5) thereof the sub-region (8,5), are displayed at the positions of the sub-region (7,5) and the sub-region (8,5), respectively.

Subsequently, the numerical-value display-position determining unit 73 determines the numerical-value display position in a sub-region other than the unique region (hereinafter referred to as standard region). In this embodiment, a sub-region (i,j) where the condition of the representative value BG (i,j)≤the threshold value BG, which is the signal ratio condition, is not satisfied, that is, a sub-region (i,j) satisfying the representative value BG (i,j)>the threshold value BG1 is the standard region.

The numerical-value display-position determining unit 73 determines, as a specific region, a region that includes the standard region and that is broader than the single standard region to be the numerical-value display position. In the specific region, a single numerical value of the oxygen saturation level is displayed. In this embodiment, the specific region is a region having an area that is specific times as large as the standard region. The specific region may be any times as large as a sub-region (i,j) that is the standard region, depending on the number of numerical values of the oxygen saturation level to be displayed. Since the specific region is the numerical-value display position, in a case in which a smaller number of numerical values of the oxygen saturation level is desired to be displayed, the number of sub-regions (i,j) included in the specific region is set to a smaller number.

Figure 10:
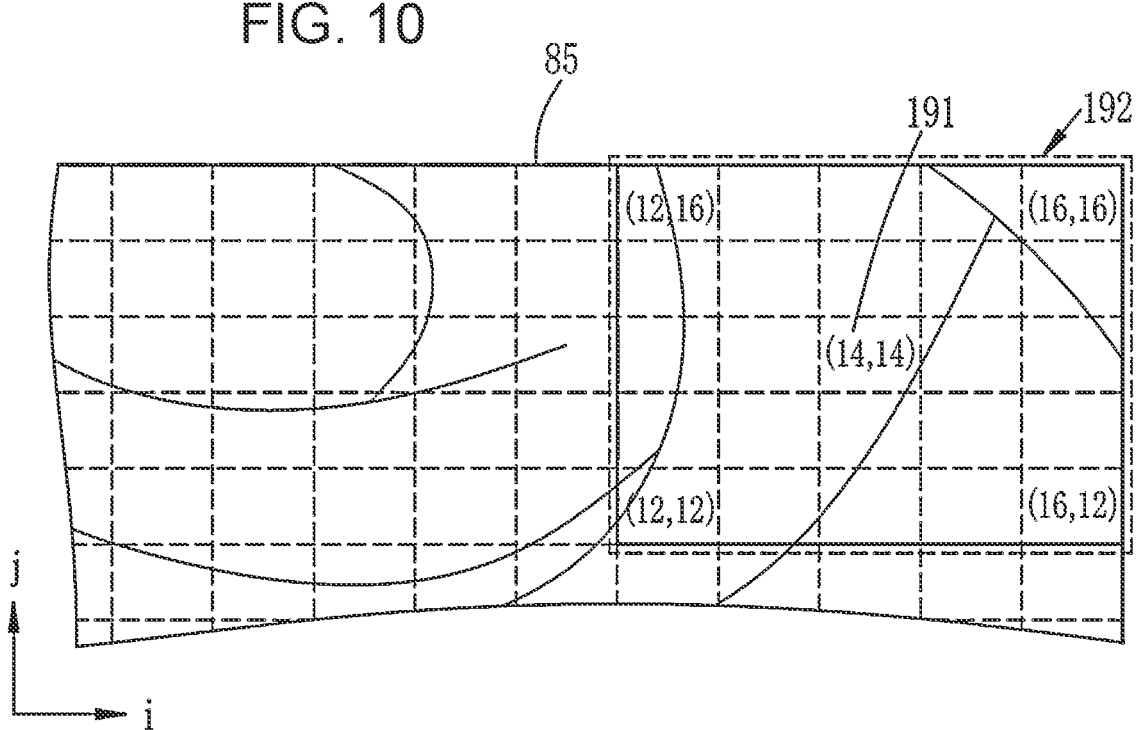
FIG. 10 is an explanation diagram illustrating a specific region.

In this embodiment, the specific region is a substantially square region corresponding to 25 sub-regions, which is five times in height and five times in width as large as the standard region. Thus, more specifically, as illustrated in FIG. 10, a specific region 192 is set as a square area in which the center is the sub-region (14,14), which is a standard region 191, and in which the vertexes are four points of the sub-region (12,12), the sub-region (16,12), the sub-region (16,16), and the sub-region (12,16). The specific region 192 is a first specific region.

Figure 11:
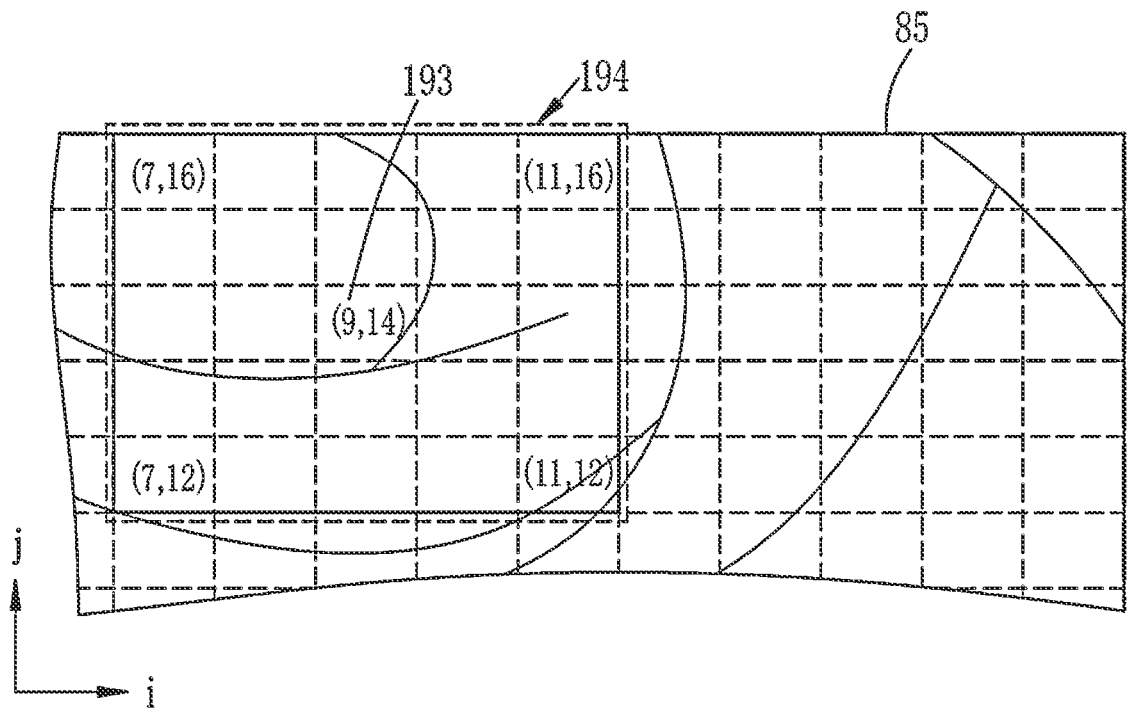
FIG. 11 is an explanation diagram illustrating setting of the specific region.

Note that the standard region 191 belongs to the single specific region 192 and is set not to belong to two or more specific regions. This is because, as the specific region is the numerical-value display position, the numerical values of the oxygen saturation level are to be displayed at appropriate intervals. Thus, as illustrated in FIG. 11, a specific region 194 is set including a standard region 193 at the center so as to be adjacent to the specific region 192 without the specific regions overlapping with each other. Thus, the specific region 194 is set as a square area in which the center is the sub-region (9,14), which is the standard region 193, and in which the vertexes are four points of the sub-region (7,12), the sub-region (11,12), the sub-region (11,16), and the sub-region (7,16). This specific region is a second specific region.

In the setting of a specific region, if total peripheral standard regions are not a substantially square region corresponding to 25 sub-regions (i,j), the regions may not be set as a specific region or may be set as a specific region, for example, on the assumption that there are sub-regions to corresponding to 25 sub-regions to be a substantially square region.

Next, the numerical value of the oxygen saturation level to be displayed in a sub-region will be described. In this embodiment, the numerical value of the oxygen saturation level displayed in the specific region is the average value SP of the oxygen saturation level calculated in all the pixels included in the sub-regions (i,j) included in the specific region. Thus, since the specific region is set as 25 sub-regions (i,j), the average value SP of the oxygen saturation level calculated in all the pixels included in the 25 sub-regions (i,j) is the numerical value of the oxygen saturation level to be displayed in the specific region.

A table 196 in FIG. 13 illustrates the position of the specific region (column "specific region position" in the table 196) and the average value SP of the oxygen saturation level (column "SP (n-th)" in the table 196). For example, the numerical value 99, which is the average value SP (first) of the oxygen saturation level in the first specific region, is displayed at the position of the first specific region. For the average value SP (second) in the second specific region, the oxygen saturation level is not displayed ("−" in the SP (n-th) column in the table 196) because it is determined as a distant view at the time of image processing or the numerical value of the oxygen saturation level has become greater than or equal to 100% or less than or equal to 0%, for example.

On the basis of the numerical-value display position of the numerical value of the oxygen saturation level determined by the numerical-value display-position determining unit 73, the display control unit 66 displays the numerical value of the oxygen saturation level on the oxygen-saturation-level image. The method of displaying the numerical value of the oxygen saturation level in the unique region can be freely set. For example, at the center of the sub-regions (i,j) that are the unique region, the numerical value of the oxygen saturation level is displayed in a manner distinguishable from the oxygen-saturation-level image, for example, in a character color distinguishable from the oxygen-saturation-level image. Similarly, the method of displaying the numerical value of the oxygen saturation level in the specific region can be freely set, as in the case of the unique region. For example, at the center of the specific region, the numerical value of the oxygen saturation level is displayed in a manner distinguishable from the oxygen-saturation-level image, in a character color distinguishable from the oxygen-saturation-level image. Note that the display manner of the numerical value of the oxygen saturation level in the unique region and in the specific region may be the same or different from each other as long as it is easy to view.

Figure 14:
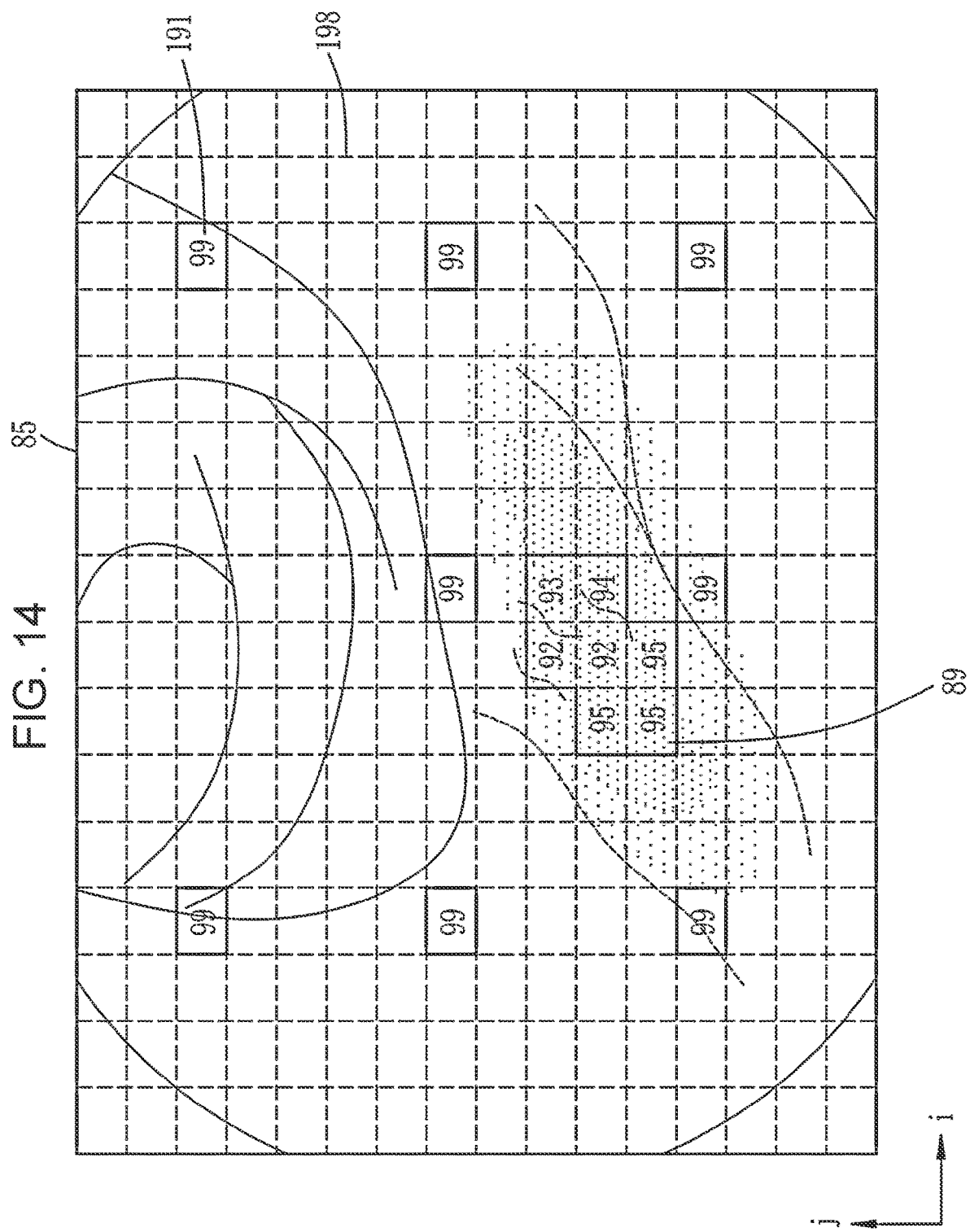
FIG. 14 is an explanation diagram illustrating numerical-value display positions based on the signal ratio condition.

On the basis of the unique region and the specific region each of which is the numerical-value display position of the numerical value of the oxygen saturation level determined by the numerical-value display-position determining unit 73 and the numerical value of the oxygen saturation level for display, the display control unit 66 displays the numerical value of the oxygen saturation level on the oxygen-saturation-level image. In this embodiment, examples of the numerical values of the oxygen saturation level displayed by the display control unit 66 on the oxygen-saturation-level image will be described with reference to FIG. 14. On the oxygen-saturation-level image 85, the unique region 89 is a part of sub-regions surrounded by a solid line, and in each sub-region, the numerical value of the oxygen saturation level in the sub-region is displayed. In addition, standard regions 191, each of which is a center part of a specific region, are parts surrounded by solid lines, in which the numerical value of the oxygen saturation level in the specific region is displayed. Note that only one of the standard regions 191 that are the centers of specific regions is denoted by reference numeral 191 to avoid complexity of the figure.

Figure 15:
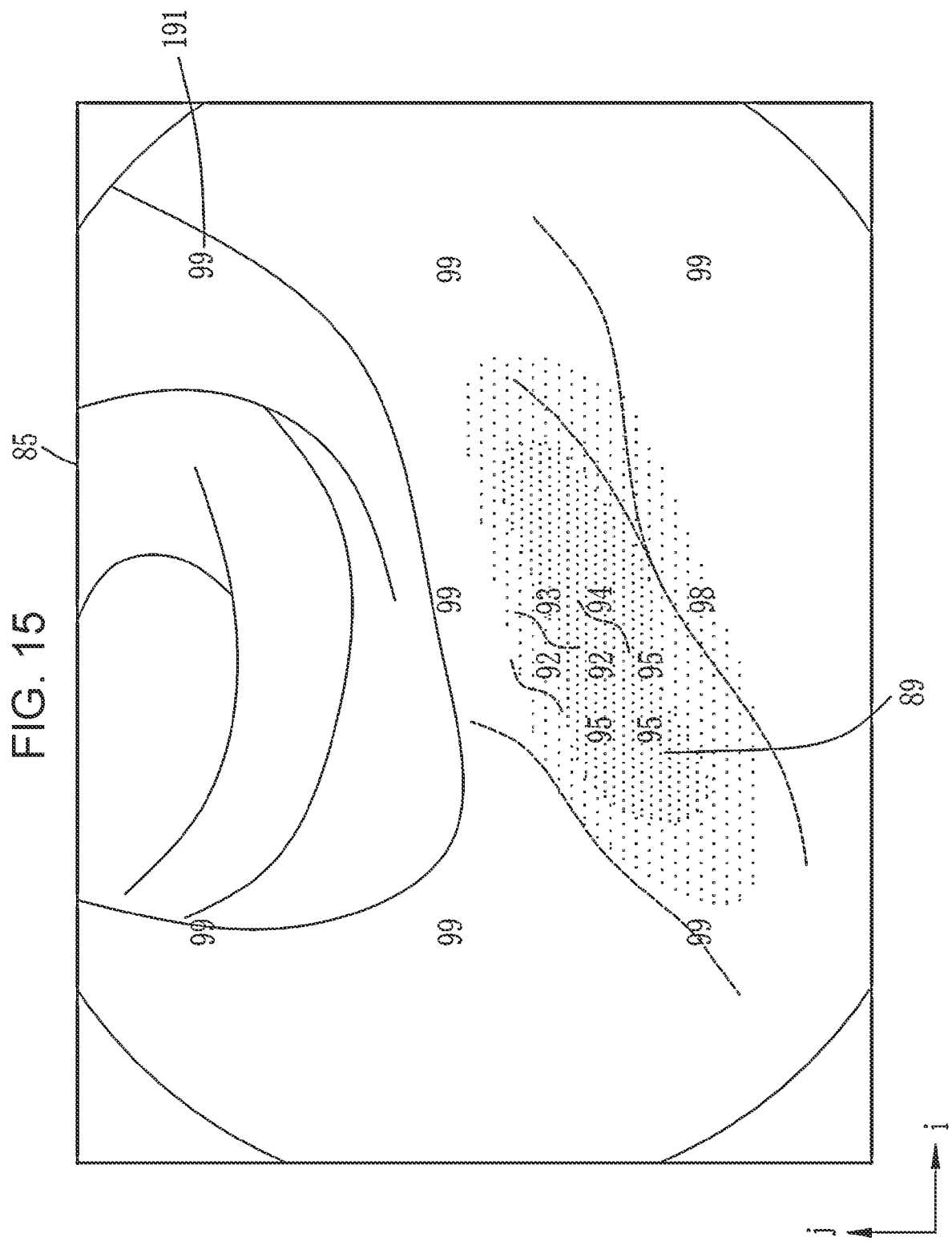
FIG. 15 is an explanation diagram of the oxygen-saturation-level image in which numerical values are displayed on the basis of the signal ratio condition.

As illustrated in FIG. 15, on the monitor 18, an image displaying the numerical values of the oxygen saturation level on the oxygen-saturation-level image is displayed in a manner that a grid 198 (see FIG. 14) illustrating sub-regions is not displayed. Note that the grid 198 (see FIG. 14) may also be displayed on the monitor 18 in response to an instruction in order to adjust the number of numerical values of the oxygen saturation level to be displayed or to grasp the part in which a displayed oxygen saturation level is the average.

Note that the oxygen-saturation-level image and the numerical values of the oxygen saturation level displayed on the monitor 18 are sequentially updated each time an oxygen-saturation-level image is created. Thus, although a moving image is displayed on the monitor 18 by updating of the oxygen-saturation-level image, in order to prevent the numerical values of the oxygen saturation level from changing one after another, the numerical values of the oxygen saturation level may be displayed without updating for a certain period, and the most recent numerical values of the oxygen saturation level may be displayed at the time of updating.

Figure 16:
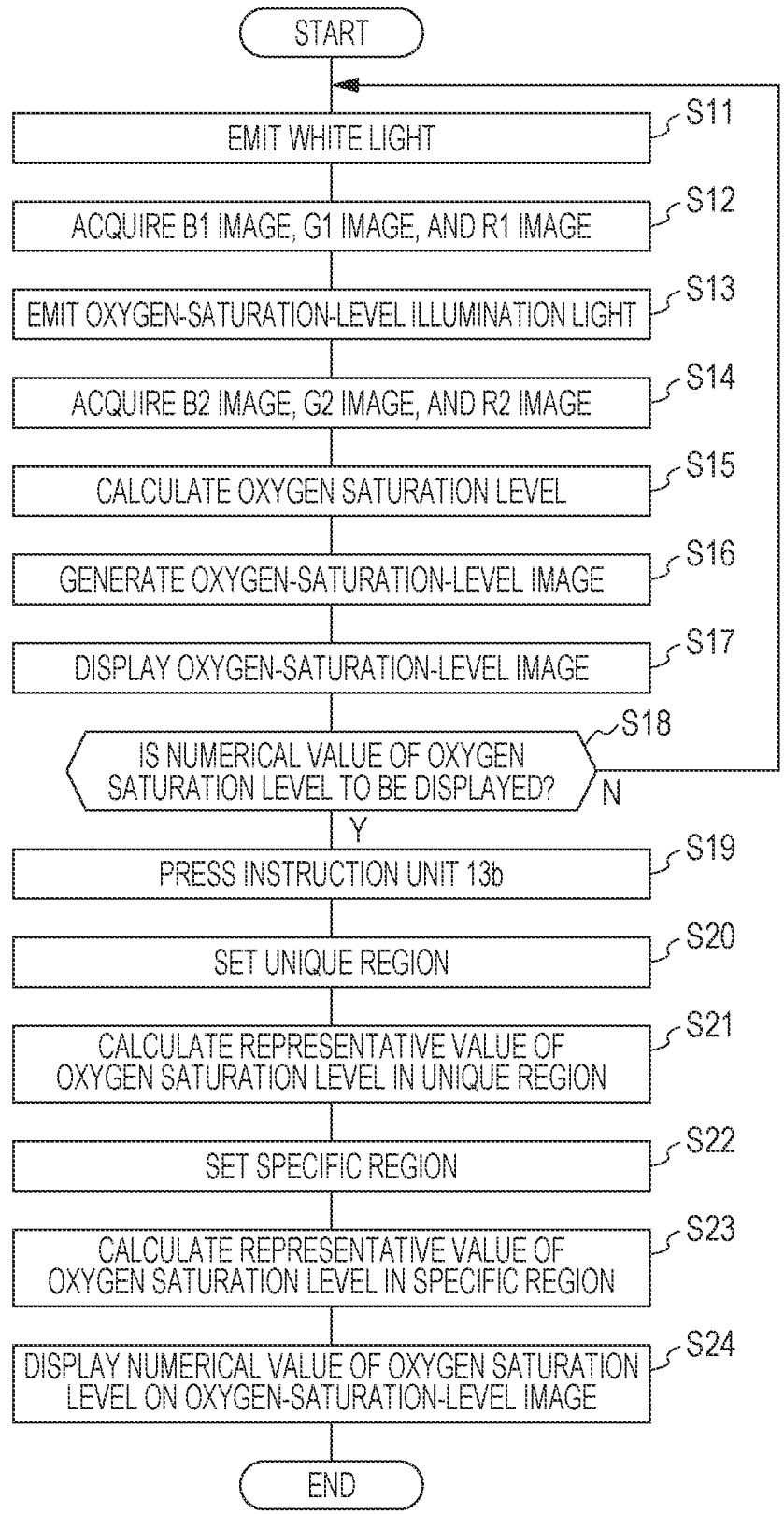
FIG. 16 is a flowchart illustrating a flow of an image processing unit.

Next, a flow of displaying the numerical value of the oxygen saturation level on the oxygen-saturation-level image in the oxygen-saturation-level observation mode in this embodiment will be described with reference to FIG. 16. First, the light source unit 20 generates white light by using the first light emission pattern and irradiates the observation target with the generated white light (S11). The image sensor 48 images the observation target irradiated with the white light, and the image acquiring unit 54 acquires spectral images of a B1 image signal, a G1 image signal, and an R1 image signal (S12).

Subsequently, the light source unit 20 generates illumination light for oxygen saturation level observation, which is mixed color light of the second blue light BL, the green light G, and the red light R, by using the second light emission pattern and irradiates the observation target with the generated mixed color light of the second blue light BL, the green light G, and the red light R (S13). The image sensor 48 images the observation target irradiated with the mixed color light of the second blue light BL, the green light G, and the red light R. Then, the image acquiring unit 54 acquires spectral images of a B2 image signal, a G2 image signal, and an R2 image signal (S14).

Subsequently, by using the B2 image signal, the G1 image signal, and the R1 image signal, the oxygen-saturation-level calculating unit 70 calculates the oxygen saturation level by referring to an LUT in the data storage unit 71 (S15). Then, the image creating unit 72 generates an oxygen-saturation-level image that is an image representing the oxygen saturation level (S16). The display control unit 66 sequentially displays generated oxygen-saturation-level images on the monitor 18 (S17).

In the oxygen-saturation-level observation mode, an operator observes the oxygen-saturation-level image displayed on the monitor 18. If the operator desires to check the oxygen saturation level more specifically, to cause the numerical value of the oxygen saturation level to be displayed on the oxygen-saturation-level image (Y in S18), the operator presses the instruction unit 13b of the endoscope 12 once (S19). In response to an instruction from the instruction unit 13b, the numerical-value display-position determining unit 73 automatically performs a series of processes to display the numerical value of the oxygen saturation level on the oxygen-saturation-level image. First, the numerical-value display-position determining unit 73 determines the display position of the numerical value of the oxygen saturation level in a stepwise manner First, to display the numerical value of the oxygen saturation level in the assumed region of interest, for each sub-region obtained by dividing of the oxygen-saturation-level image in a grid shape, a sub-region (unique region) in which the superficial blood vessel density corresponds to the preset signal ratio condition is set (S20). Then, the representative value of the oxygen saturation level in the unique region is calculated (S21). Subsequently, a sub-region other than the unique region is set as the specific region (S22). Then, the representative value of the oxygen saturation level in the specific region is calculated (S23). An image (FIG. 15) in which the numerical values of the oxygen saturation level are appropriately displayed on the oxygen-saturation-level image is displayed on the monitor 18 (S24). Note that, if the operator does not desire to display the numerical value of the oxygen saturation level (N in S18), the process returns to emission of the white light (S11), and the oxygen-saturation-level image is updated.

Second Embodiment

This embodiment is substantially the same as the first embodiment except that the assumed region of interest is a region in which the oxygen saturation level locally differs. The region in which the oxygen saturation level locally differs is, for example, a low-oxygen region due to cancer. Thus, the numerical-value display-position determining unit 73 calculates the representative value of the oxygen saturation level in a sub-region, and, if the representative value satisfies an oxygen-saturation-level condition, determines the sub-region to be the numerical-value display position as a local region. The numerical-value display-position determining unit 73 determines each sub-region to be the local region or not. In a sub-region determined as the local region, a single numerical value of the oxygen saturation level is displayed.

To determine the numerical-value display position in the local region, the numerical-value display-position determining unit 73 calculates a representative value SO (i,j) of the oxygen saturation level for each of all sub-regions (i,j), and, if the representative value SO (i,j) of the oxygen saturation level satisfies the oxygen-saturation-level condition, determines the sub-region as the local region.

Figure 17:
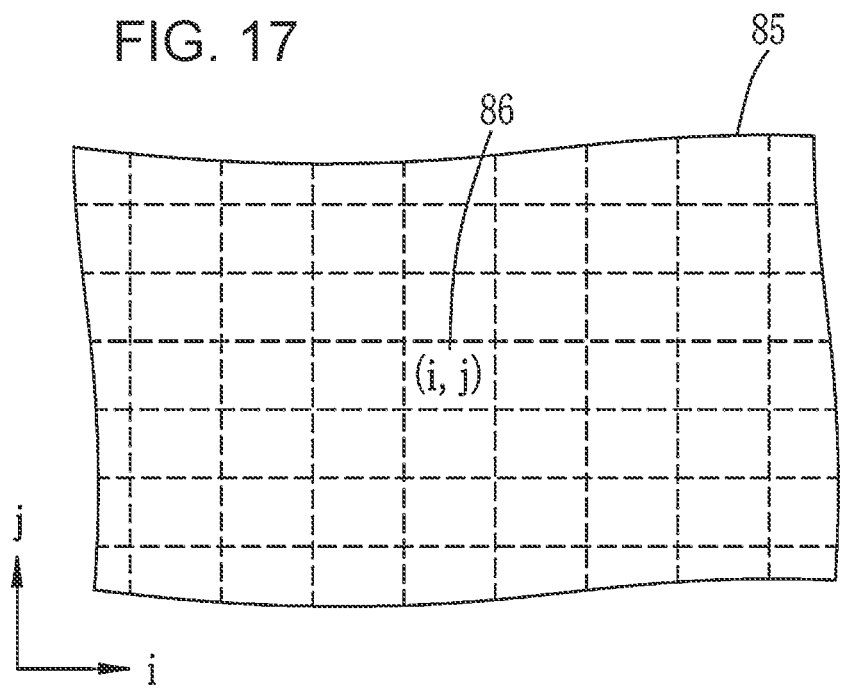
FIG. 17 is an explanation diagram illustrating an oxygen-saturation-level condition.

The representative value SO (i,j) is determined as follows. That is, as illustrated in FIG. 17, the numerical values of the oxygen saturation level are calculated in all the pixels that a sub-region (i,j) 86 has in the oxygen-saturation-level image 85, and the average value of these numerical values of the oxygen saturation level is calculated and set as the representative value SO (i,j) of the oxygen saturation level in the in the sub-region (i,j).

The oxygen-saturation-level condition is that the representative value of the oxygen saturation level is greater than the oxygen saturation level in the periphery of the sub-region by a specific value or more, or is less than that by a specific value or more. Thus, the representative value SO (i,j) and the numerical value of the oxygen saturation level in a sub-region in the periphery is compared with each other, and, if the representative value SO (i,j) is greater than the oxygen saturation level in a region in the periphery of the sub-region (i,j) by a specific value or more, or is less than that by a specific value or more, or both, since the oxygen-saturation-level condition is satisfied, the sub-region is set as the local region. Note that the specific values herein may be the same or different from each other.

Figure 18:
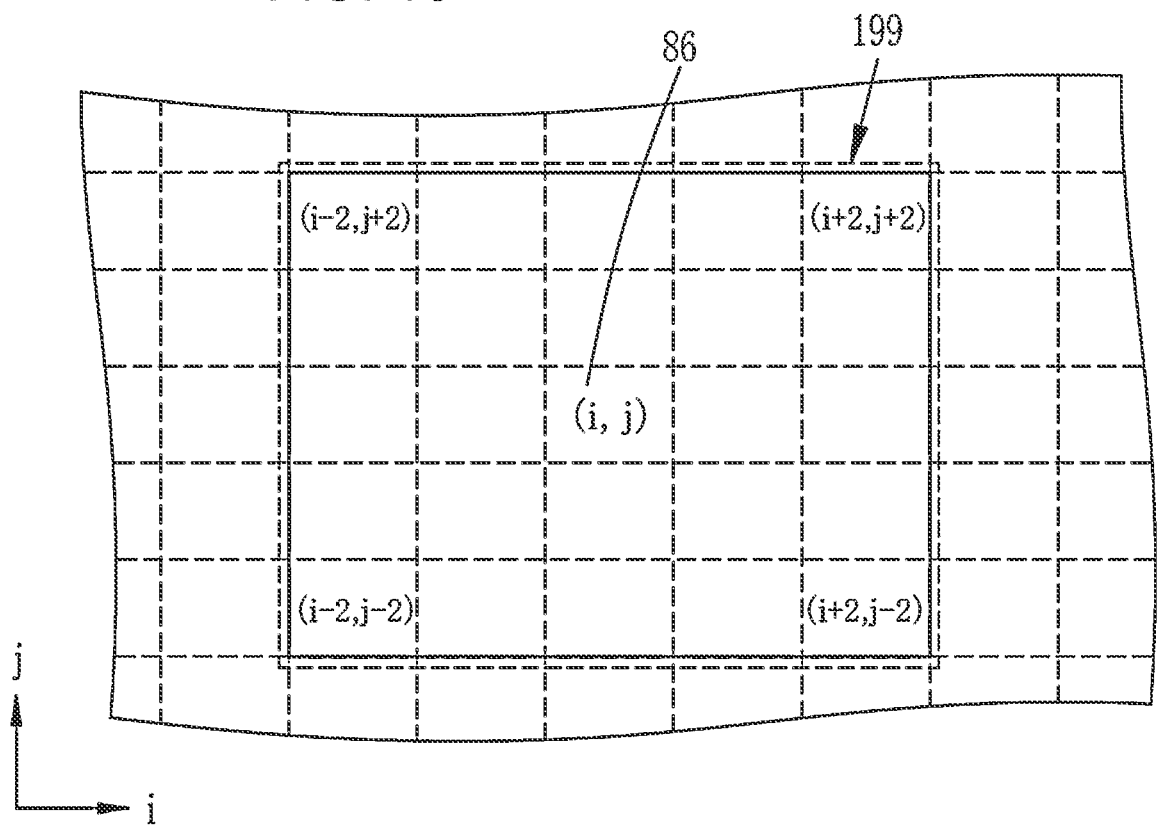
FIG. 18 is an explanation diagram illustrating a peripheral region.

In this embodiment, as the region in the periphery of the sub-region (i,j), a region that includes the sub-region (i,j) and that is broader than the single sub-region (i,j) is set as a peripheral region. In this embodiment, a region having an area that is specific times as large as the single sub-region (i,j) is set as the peripheral region. The peripheral region may be any times as large as the sub-region (i,j), depending on the case. As illustrated in FIG. 18, in this embodiment, a peripheral region 199 is a substantially square region corresponding to 25 sub-regions, which is five times in height and five times in width as large as the sub-region (i,j) 86. Thus, the peripheral region 199 is set as a square area in which the center is the sub-region (i,j) 86 and in which the vertexes are four points of the sub-region (i−2,j−2), the sub-region (i+2,j−2), the sub-region (i+2,j+2), and the sub-region (i−2,j+2). Note that, if regions in the periphery of any given sub-region (i,j) 86 are insufficient for the peripheral region 199 corresponding to 25 sub-regions, an adjacent region is copied and used.

As the specific value, in this embodiment, in the peripheral region of the sub-region (i,j), a value calculated from the average and the standard deviation of the representative value SO (i,j) of the oxygen saturation level is set as the specific value. Thus, the average and the standard deviation are calculated for each of 25 representative values of the oxygen saturation level in sub-regions (i,j), and, if the representative value SO (i,j) is greater than or equal to the sum of the average and the standard deviation or is less than or equal to a difference between the average and the standard deviation, the numerical-value display-position determining unit 73 determines the sub-region (i,j) to be the numerical-value display position. The numerical-value display-position determining unit 73 examines whether the oxygen-saturation-level condition is satisfied in all sub-regions (i,j).

Figure 19:
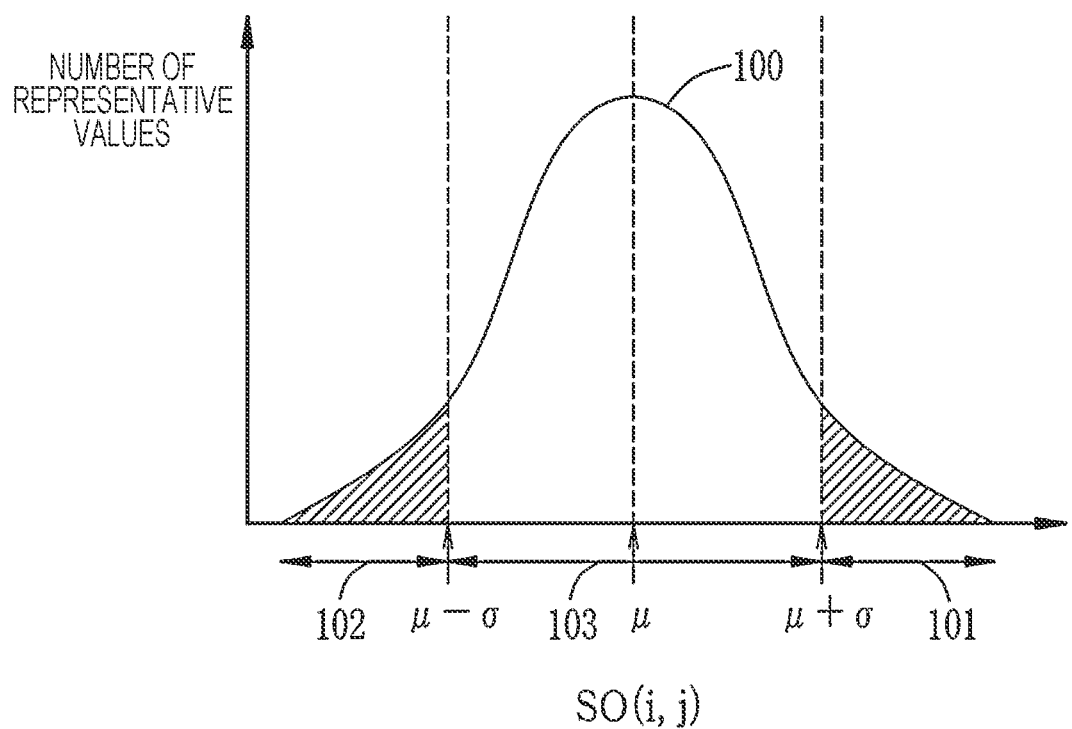
FIG. 19 is a graph illustrating the oxygen-saturation-level condition.

As illustrated in FIG. 18, more specifically, in 25 sub-regions included in the peripheral region 199 of the sub-region (i,j), for each sub-region, the representative value SO (i,j) of the oxygen saturation level is calculated. An average μ and a standard deviation σ are calculated for the calculated 25 representative values SO (i,j) of the oxygen saturation level. As illustrated in FIG. 19, in a distribution curve 100 of 25 representative values SO (i,j) of the oxygen saturation levels, if a representative value SO (i,j) of the oxygen saturation level in a sub-region (i,j) is away from the average μ by the standard deviation σ or more, the oxygen-saturation-level condition is satisfied. Note that the X-axis of the distribution curve 100 is the value of the representative value SO (i,j), and the Y-axis is the number of representative values SO (i,j). Thus, a case in which the representative value SO (i,j) of the oxygen saturation level in the sub-region (i,j) is greater than or equal to a specific value, which is the average μ+the standard deviation σ, corresponds to an oxygen-saturation-level condition corresponding value 101, and thus, this sub-region (i,j) is determined to be the numerical-value display position as the local region (the right shaded area in FIG. 19). Similarly, also a case in which the representative value SO (i,j) of the oxygen saturation level in the sub-region (i,j) is less than or equal to a specific value, which is the average μ−the standard deviation σ, corresponds to an oxygen-saturation-level condition corresponding value 102, and thus, this sub-region (i,j) is determined to be the numerical-value display position as the local region (the left shaded area in FIG. 19).

The numerical value of the oxygen saturation level displayed in the local region is, in this embodiment, as in the first embodiment, the average value of the oxygen saturation level calculated in all the pixels included in the sub-region (i,j) that is the local region.

Subsequently, the numerical-value display-position determining unit 73 determines the numerical-value display position in the standard region, which is a region other than the local region. That is, the numerical-value display-position determining unit 73 determines the numerical-value display position in a sub-region (i,j) other than the sub-region (i,j) that is determined to be the numerical-value display position as the local region. In this embodiment, the sub-region (i,j) other than the local region is, if the representative value SO (i,j) of the oxygen saturation level in FIG. 19 is not away from the average µ by the standard deviation σ and exists in an oxygen-saturation-level condition non-corresponding value 103 (µ−σ<representative value SO (i,j)<µ+σ), the standard region that does not correspond to the oxygen-saturation-level condition.

Thus, according to this embodiment, since, on the basis of the oxygen-saturation-level condition, a region in which the representative value of the oxygen saturation level is greater than the oxygen saturation level in a periphery of the sub-region by a specific value or more, or is less than that by a specific value or more is determined to be the numerical-value display position, a region in which the oxygen saturation level locally differs can be determined to be the numerical-value display position, and the numerical value of the oxygen saturation level can be displayed. The method of determining the numerical-value display position in the standard region is substantially the same as in the first embodiment.

Figure 20:
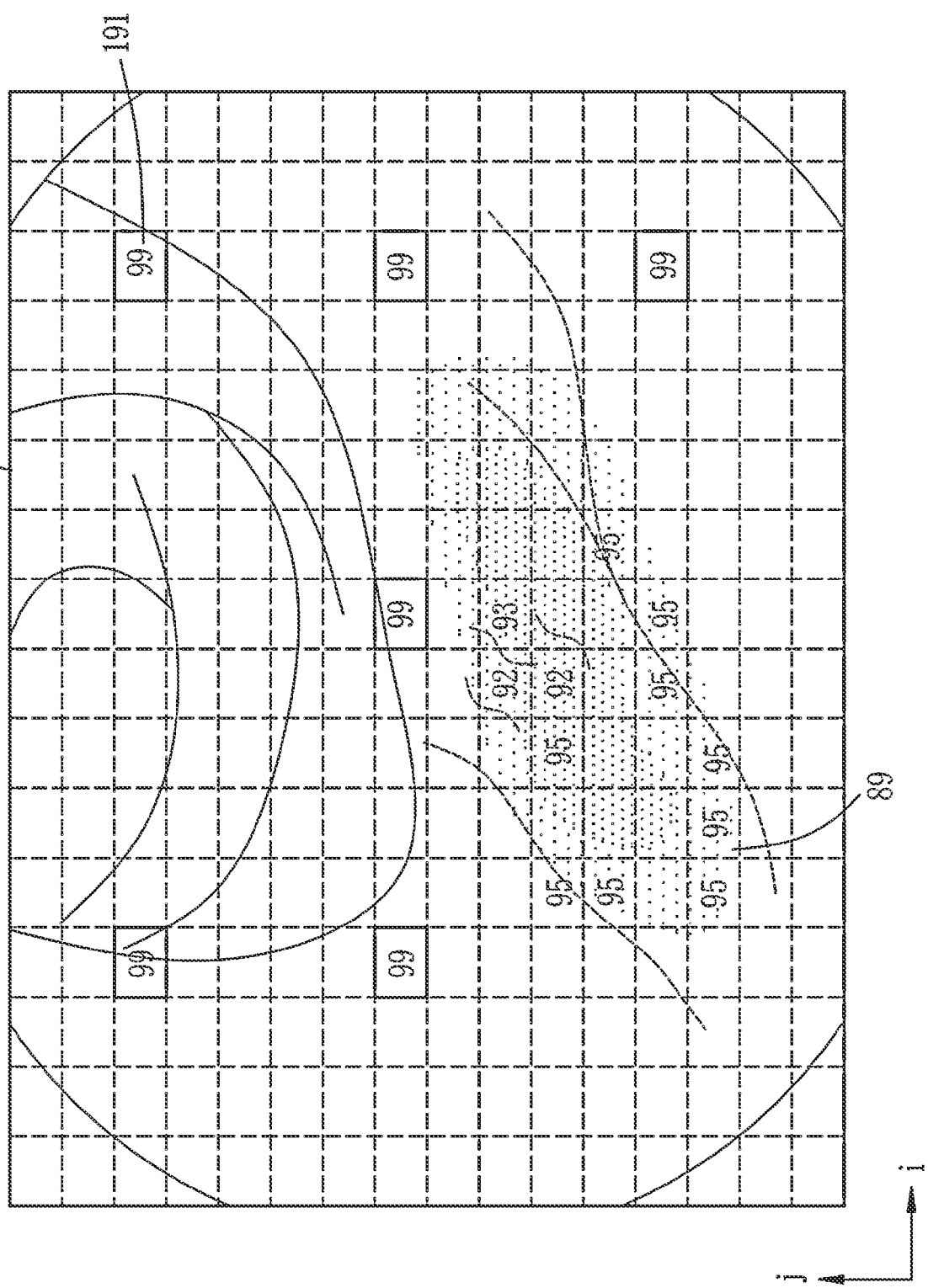
FIG. 20 is an explanation diagram illustrating numerical-value display positions based on the oxygen-saturation-level condition.
Figure 21:
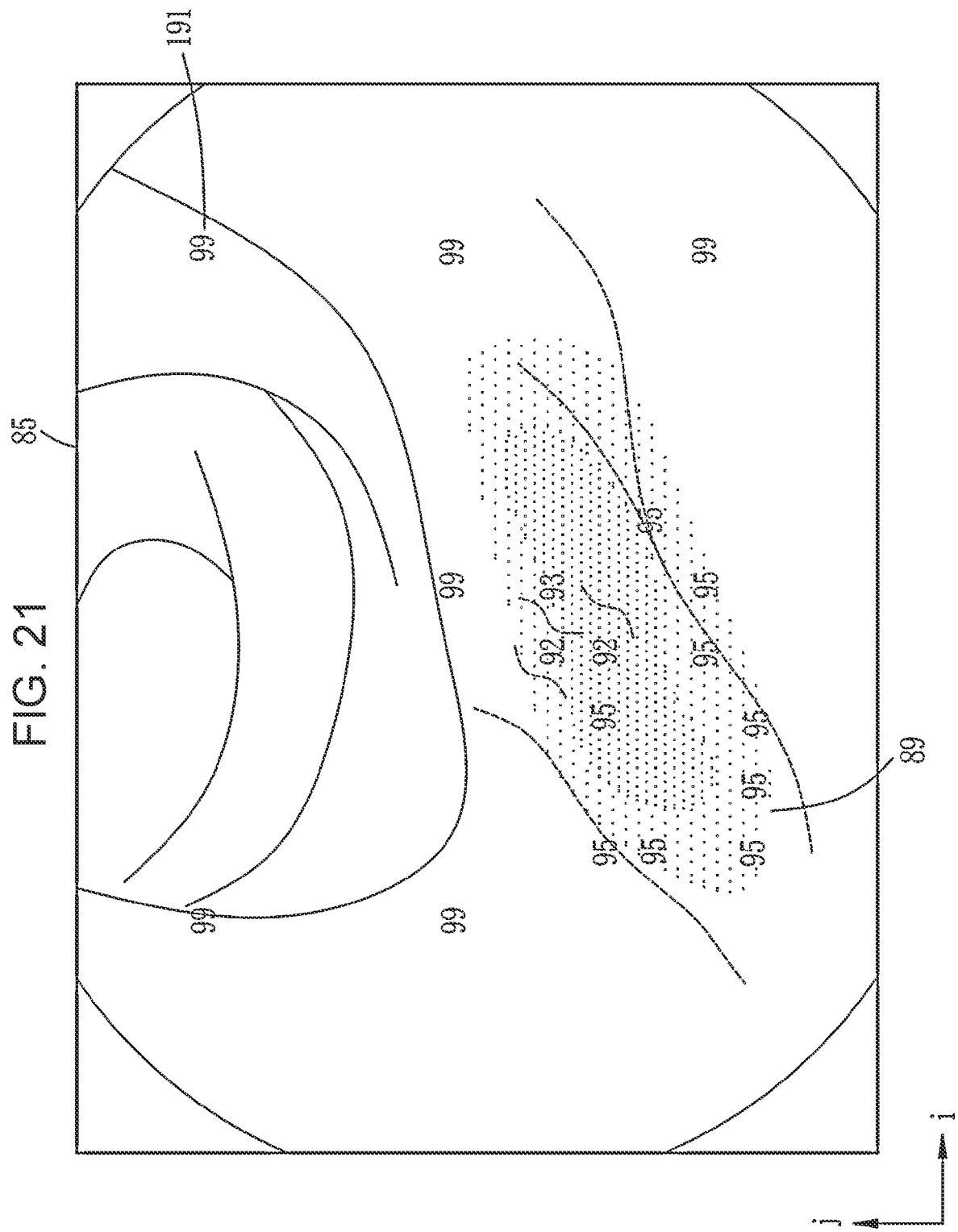
FIG. 21 is an explanation diagram of the oxygen-saturation-level image in which numerical values are displayed on the basis of the oxygen-saturation-level condition.

As in the first embodiment, on the basis of the numerical-value display position of the numerical value of the oxygen saturation level determined by the numerical-value display-position determining unit 73, the display control unit 66 displays the numerical value of the oxygen saturation level on the oxygen-saturation-level image. In this embodiment, on the basis of the local region and the specific region each of which is the numerical-value display position of the numerical value of the oxygen saturation level determined by the numerical-value display-position determining unit 73 and the numerical value of the oxygen saturation level for display, the display control unit 66 displays the numerical value of the oxygen saturation level on the oxygen-saturation-level image. Examples of the numerical value of the oxygen saturation level are illustrated in FIG. 20. In this embodiment, the local region is the unique region 89 and a region other than the local region is the standard region. On the oxygen-saturation-level image 85, in the unique region 89, in each sub-region, a representative value of the oxygen saturation level in the sub-region is displayed. In addition, standard regions 191, each of which is a center part of a specific region, are parts in which a single sub-region is surrounded by solid lines, in which the numerical value of the oxygen saturation level in the specific region is displayed. Note that only one of the unique regions 89 and only one of the standard regions 191 that are the centers of specific regions are denoted by reference numerals to avoid complexity of the figure. Furthermore, as illustrated in FIG. 21, on the monitor, an image displaying the numerical values of the oxygen saturation level on the oxygen-saturation-level image is displayed in a manner that the grid 198 (see FIG. 14) illustrating sub-regions is not displayed.

Third Embodiment

This embodiment is substantially the same as the first embodiment or the second embodiment except that the assumed region of interest is a region in which the superficial blood vessel density is high and is also a region in which the oxygen saturation level locally differs. Thus, as in the first embodiment or the second embodiment, the numerical-value display-position determining unit 73 determines the display position of the numerical value of the oxygen saturation level in a stepwise manner First, in a region in which the superficial blood vessel density is high and in a region in which the oxygen saturation level locally differs, the numerical-value display position is determined (AND unique region), and, in a region other than the region determined to be the numerical-value display position, that is, a region other than the AND unique region (standard region), the numerical-value display position is determined. Thus, the AND unique region is the AND of the region in which the superficial blood vessel density is high and the region in which the oxygen saturation level locally differs, and the standard region is a region that is the XOR of the region in which the superficial blood vessel density is high and the region in which the oxygen saturation level locally differs.

As in the first embodiment, in all sub-regions (i,j), the numerical-value display-position determining unit 73 calculates a representative value of the signal ratio indicating a pixel value ratio between different spectral images, which are the B1 image and the G1 image, examines whether the signal ratio satisfies the signal ratio condition, and determines a sub-region (i,j) in which the signal ratio condition is satisfied. In addition, as in the second embodiment, in all sub-regions (i,j), the numerical-value display-position determining unit 73 examines whether a representative value of the oxygen saturation level satisfies the oxygen-saturation-level condition, and determines a sub-region (i,j) in which the oxygen-saturation-level condition is satisfied. Since the AND unique region is the AND of the region in which the superficial blood vessel density is high and the region in which the oxygen saturation level locally differs, if a sub-region (i,j) corresponds to both the signal ratio condition and the oxygen-saturation-level condition, the sub-region (i,j) is determined to be the AND unique region, and the AND unique region is determined to be the numerical-value display position.

Subsequently, in the standard region that is a region other than the AND unique region, the numerical-value display-position determining unit 73 determines the numerical-value display position. In this embodiment, since the standard region is the XOR of the region in which the superficial blood vessel density is high and the region in which the oxygen saturation level locally differs, the standard region is any of 1) a region that is the region in which the superficial blood vessel density is high but is not the region in which the oxygen saturation level locally differs, 2) a region that is not the region in which the superficial blood vessel density is high but is the region in which the oxygen saturation level locally differs, or 3) a region that is not the region in which the superficial blood vessel density is high nor the region in which the oxygen saturation level locally differs. The method of determining the numerical-value display position in the standard region is substantially the same as in the first embodiment or the second embodiment.

Figure 22:
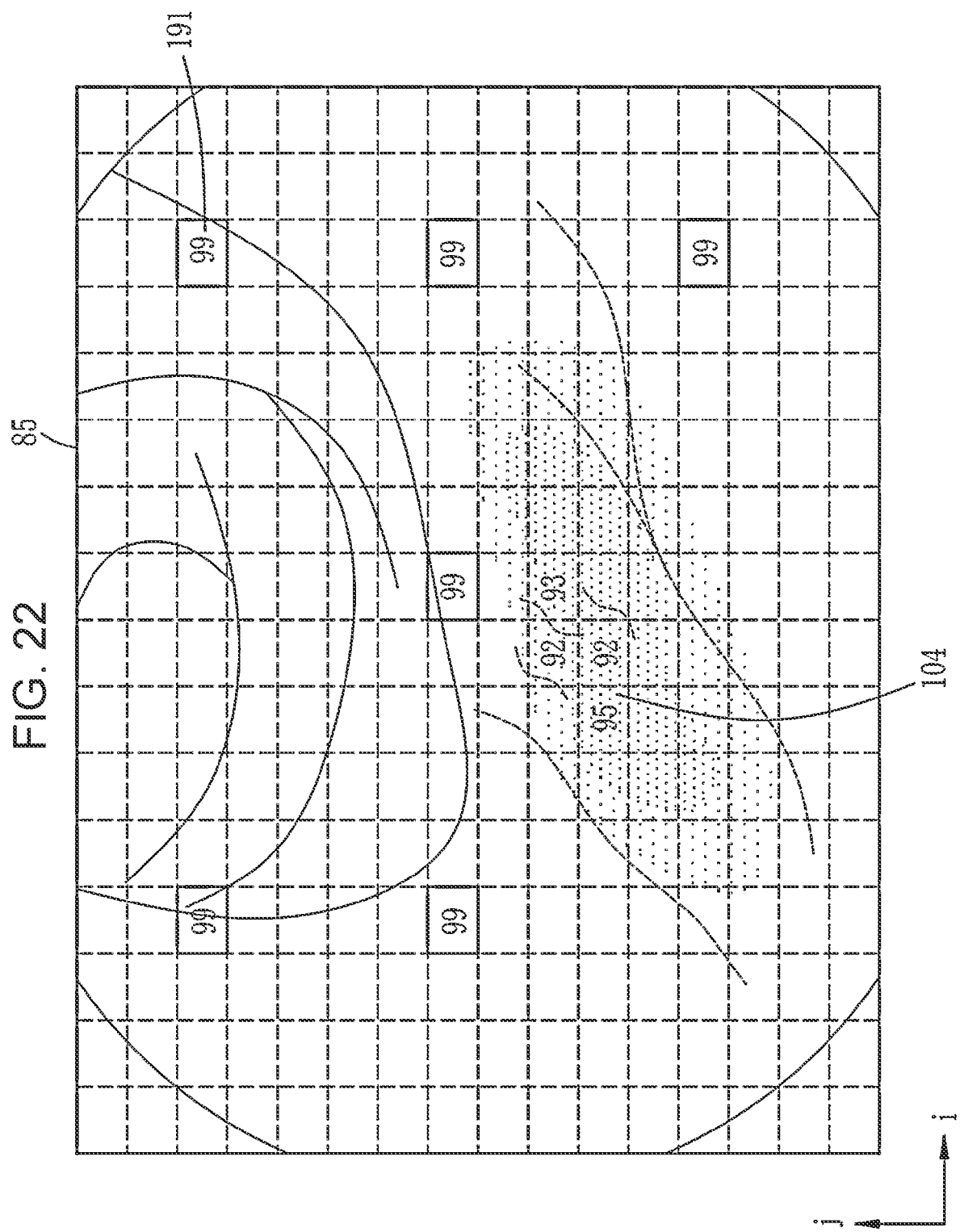
FIG. 22 is an explanation diagram illustrating numerical-value display positions based on the signal ratio condition and the oxygen-saturation-level condition.
Figure 23:
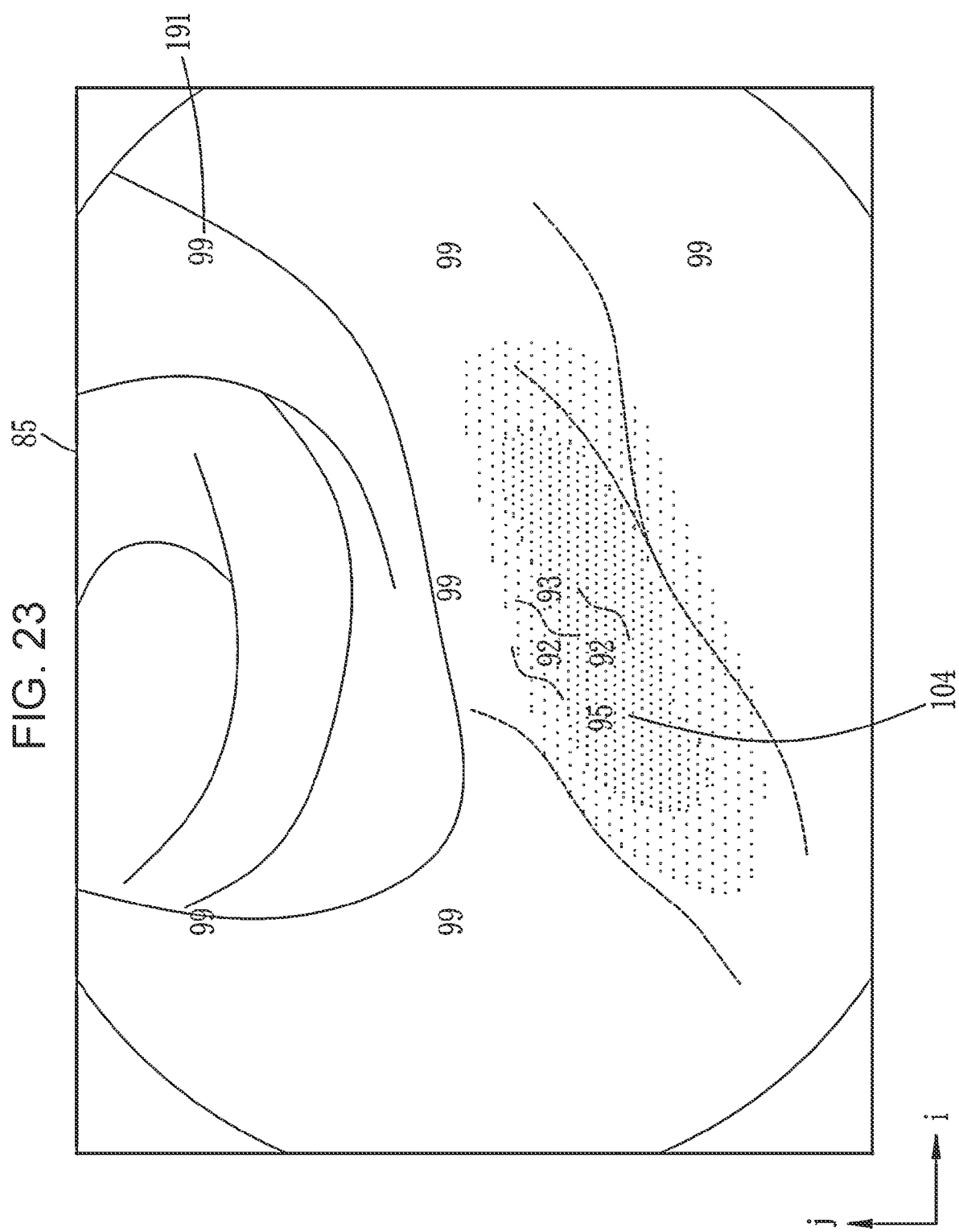
FIG. 23 is an explanation diagram of the oxygen-saturation-level image in which numerical values are displayed on the basis of the signal ratio condition and the oxygen-saturation-level condition.

As in the first embodiment or the second embodiment, on the basis of the AND unique region determined by the numerical-value display-position determining unit 73, the display control unit 66 displays the numerical value of the oxygen saturation level on an oxygen-saturation-level image. In this embodiment, FIG. 22 illustrates an example in which, on the basis of the AND unique region determined by the numerical-value display-position determining unit 73 and the numerical values of the oxygen saturation level for display, the display control unit 66 displays the numerical values of the oxygen saturation level on the oxygen-saturation-level image. The method of displaying the numerical values of the oxygen saturation level in the AND unique region and the standard region can be substantially the same as the method of displaying the numerical values of the oxygen saturation level in the first embodiment or the second embodiment. On the oxygen-saturation-level image 85, in an AND unique region 104, in each sub-region, a representative value of the oxygen saturation level in the sub-region is displayed. In addition, the center of a specific region is a part of a sub-region surrounded by a line at the position of a standard region, in which the numerical value of the oxygen saturation level in the specific region is displayed. Note that only one of the AND unique regions 104 and only one of the standard regions 191 that are the centers of specific regions are denoted by reference numerals to avoid complexity of the figure. Furthermore, as illustrated in FIG. 23, on the monitor, an image displaying the numerical values of the oxygen saturation level on the oxygen-saturation-level image is displayed in a manner that the grid 198 (see FIG. 14) illustrating sub-regions is not displayed.

By constituting the endoscope system 10 in the above manner, when displaying the numerical value of the oxygen saturation level on an oxygen-saturation-level image, as the numerical-value display position, not only a part in which the oxygen saturation level differs from that in the periphery is predominantly displayed, but also the oxygen saturation level on the entire oxygen-saturation-level image can be appropriately displayed. Thus, in an endoscope device having an oxygen saturation level imaging function, when a subtle difference in the oxygen saturation level between a lesion part and a normal part is desired to be evaluated, it is possible to observe the oxygen saturation level distribution and grasp specific numerical values at the same time unlike in a case of displaying the high and low oxygen saturation levels with pseudo-colors. In addition, since the oxygen saturation level is displayed in the form of a numerical value, the oxygen saturation level itself can be grasped in detail, and also, a difference from the periphery can be grasped in detail. Furthermore, the specific numerical value of the oxygen saturation level enables estimation of the degree of a symptom or the like.

Since the numerical value of the oxygen saturation level as above is automatically displayed in response to a simple operation by an operator, such as pressing of a button on a scope, the operation can be prevented from being complex. That is, in response to a simple operation by an operator of an endoscope, such as pressing of a button, the numerical value is displayed on the oxygen-saturation-level image in an overlapping manner, in an assumed region of interest in which the value of the oxygen saturation level or the blood vessel structure differs from that in the periphery. In addition, also in a region with subtle characteristics other than the assumed region of interest, numerical values are displayed at appropriate intervals, and it is possible to observe the oxygen saturation level distribution and grasp specific numerical values at the same time.

In addition, in a case in which a region in which the superficial blood vessel density is high or a region in which the oxygen saturation level locally differs is selected as a unique region in which the oxygen saturation level differs from that in the periphery, a lesion, such as cancer, can be grasped in detail. Furthermore, it is easy to judge that a part in which the numerical value of the oxygen saturation level is displayed is a region to be focused, and this can prevent a lesion from being unnoticed.

A method of operating the above endoscope system 10 includes: an image acquiring step in which an image acquiring unit acquires a plurality of spectral images obtained by imaging of an observation target; an oxygen-saturation-level calculating step in which an oxygen-saturation-level calculating unit calculates an oxygen saturation level of the observation target on the basis of the plurality of spectral images; an image creating step in which an image creating unit creates an oxygen-saturation-level image that is an image representing the oxygen saturation level; a numerical-value display-position determining step in which a numerical-value display-position determining unit determines a numerical-value display position for displaying a numerical value of the oxygen saturation level on the oxygen-saturation-level image displayed on a display unit, on the basis of either the spectral images or the oxygen saturation level, or both the spectral images and the oxygen saturation level; and a display control step in which a display control unit displays the numerical value of the oxygen saturation level on the oxygen-saturation-level image on the basis of the numerical-value display position.

A hardware structure of a processing unit that performs various processes of the control unit 52, the image acquiring unit 54, the image processing unit 61, the display control unit 66, or the like in the above embodiments is any of the following various processors. Various processors include a central processing unit (CPU) that is a general-purpose processor functioning as various processing units by executing software (programs), a graphical processing unit (GPU), a programmable logic device (PLD) that is a processor in which the circuit configuration is changeable after manufacture, such as field programmable gate array (FPGA), a dedicated electric circuit that is a processor having a circuit configuration that is specially designed to execute specific processing, such as an application specific integrated circuit (ASIC), and the like.

One processing unit may be constituted by one of these various processors, or may be constituted by a combination of two or more processors of the same type or different types (e.g., a combination of a plurality of FPGAs, a combination of a CPU and an FPGA, or a combination of a CPU and a GPU). In addition, a plurality of processing units may be constituted by one processor. As a first example for constituting a plurality of processing units as one processor, one or more CPUs and software may be combined to constitute one processor, and this processor may function as a plurality of processing units, as typified by a computer such as a client or a server. As a second example, a processor may be used that implements the functions of the entire system including a plurality of processing units as one integrated circuit (IC) chip, as typified by a system on chip (SoC) or the like. In this manner, various processing units are constituted by one or more of various processors as a hardware structure.

Furthermore, the hardware structure of these various processors is more specifically electric circuit (circuitry) obtained by combining circuit elements such as semiconductor elements.

The present invention can also be implemented by the following other form.

In a processor device of an endoscope system,
the processor device that acquires a plurality of spectral images obtained by imaging of an observation target;
calculates an oxygen saturation level of the observation target on the basis of the plurality of spectral images;
creates an oxygen-saturation-level image that is an image representing the oxygen saturation level;
determines a numerical-value display position for displaying a numerical value of the oxygen saturation level on the oxygen-saturation-level image displayed on a display unit, on the basis of either the spectral images or the oxygen saturation level, or both the spectral images and the oxygen saturation level; and performs control to display the numerical value of the oxygen saturation level on the basis of the numerical-value display position.

REFERENCE SIGNS LIST 10 endoscope system
12 endoscope
12a insertion part
12b operating unit
12c bending part
12d tip part
12e angle knob
13a mode switch
13b instruction unit
13c zoom operating unit
14 light source device
16 processor device
18 monitor
19 console
20 light source unit
20a BS light source
20b BL light source
20c G light source
20d R light source
22 light source control unit
30a illumination optical system
30b imaging optical system
41 light guide
45 illumination lens
46 objective lens
47 zoom lens
48 image sensor
52 control unit
54 image acquiring unit
56 DSP
58 noise reducing unit
59 conversion unit
61 image processing unit
62 normal processing unit
63 special processing unit
66 display control unit
70 oxygen-saturation-level calculating unit
71 data storage unit
72 image creating unit
73 numerical-value display-position determining unit
75 100% isopleth
76 0% isopleth
77 absorption characteristics of oxyhemoglobin
78 absorption characteristics of deoxyhemoglobin
85 oxygen-saturation-level image
86 sub-region
87 low-oxygen region
88 blood vessel
89 unique region
90 table
191, 193 standard region
192, 194 specific region
195 table
196 table
198 grid
199 peripheral region
100 oxygen-saturation-level representative-value distribution curve
101, 102 oxygen-saturation-level condition corresponding value
103 oxygen-saturation-level condition non-corresponding value
104 AND unique region
S11 to S24 step

What is claimed is:

1. A processor device comprising:
a processor configured to function as:
an image acquiring unit that acquires a plurality of spectral images obtained by imaging of an observation target;
an oxygen-saturation-level calculating unit that calculates an oxygen saturation level of the observation target on the basis of the plurality of spectral images;
an image creating unit that creates an oxygen-saturation-level image that is an image representing the oxygen saturation level;
a numerical-value display-position determining unit that determines a numerical-value display position for displaying a numerical value of the oxygen saturation level on the oxygen-saturation-level image displayed on a display, on the basis of either the spectral images or the oxygen saturation level, or both the spectral images and the oxygen saturation level; and
a display control unit that performs control to display the numerical value of the oxygen saturation level on the basis of the numerical-value display position,
wherein, for each of a plurality of regions obtained by dividing of the oxygen-saturation-level image, the numerical-value display-position determining unit determines whether the region is the numerical-value display position,
wherein, if the numerical-value display-position determining unit determines the region not to be the numerical-value display position, the numerical-value display-position determining unit determines a specific region that includes the region and that is broader than the region to be the numerical-value display position, and
wherein the specific region includes a plurality of the regions adjacent to the region that is determined not to be the numerical-value display position, and the specific regions do not overlap each other.

2. The processor device according to claim 1, wherein the regions are formed by dividing of the oxygen-saturation-level image in a grid shape.

3. The processor device according to claim 1, wherein the numerical-value display-position determining unit calculates a representative value of a signal ratio indicating a pixel value ratio between different spectral images for each of the regions, and, if the representative value of the signal ratio satisfies a signal ratio condition, determines the region to be the numerical-value display position.

4. The processor device according to claim 1, wherein the numerical-value display-position determining unit calculates a representative value of the oxygen saturation level in the region, and, if the representative value of the oxygen saturation level satisfies an oxygen-saturation-level condition, determines the region to be the numerical-value display position.

5. The processor device according to claim 1, wherein the numerical-value display-position determining unit calculates a representative value of a signal ratio indicating a pixel value ratio between different spectral images for each of the regions and calculates a representative value of the oxygen saturation level in the region, and, if the representative value of the signal ratio satisfies a signal ratio condition, and if the representative value of the oxygen saturation level satisfies an oxygen-saturation-level condition, determines the region to be the numerical-value display position.

6. The processor device according to claim 3,
wherein the signal ratio condition is that the representative value of the signal ratio is greater than or equal to a signal ratio threshold value or less than or equal to the signal ratio threshold value.

7. The processor device according to claim 4,
wherein the oxygen-saturation-level condition is that the representative value of the oxygen saturation level is greater than the oxygen saturation level in a periphery of the region by a specific value or more, or is less than the oxygen saturation level in a periphery of the region by a specific value or more.

8. An endoscope system comprising:
the processor device according to claim 1; and
a light source configured to irradiate the observation target with first illumination light and second illumination light with different spectral characteristics,
wherein the image acquiring unit acquires a first image signal corresponding to the first illumination light and acquires a second image signal corresponding to the second illumination light whose wavelength range is different from a wavelength range of the first illumination light.

9. The endoscope system according to claim 8,
wherein the second illumination light includes different absorption wavelength light for which an absorption coefficient differs between oxyhemoglobin and deoxyhemoglobin.

* * * * *